United States Patent [19]

Clarke et al.

[11] Patent Number: 4,629,319

[45] Date of Patent: Dec. 16, 1986

[54] PANEL SURFACE FLAW INSPECTION

[75] Inventors: Donald A. Clarke; Rodger L. Reynolds, both of Windsor; Timothy R. Pryor, Tecumseh, all of Canada

[73] Assignee: Diffracto Ltd., Windsor, Canada

[21] Appl. No.: 579,971

[22] Filed: Feb. 14, 1984

[51] Int. Cl.[4] .......................................... G01N 21/88
[52] U.S. Cl. ................................. 356/237; 356/446
[58] Field of Search ............... 356/237, 372, 376, 388, 356/389, 391, 420, 445, 446

[56] References Cited

U.S. PATENT DOCUMENTS

| | | |
|---|---|---|
| 2,798,966 | 7/1957 | Summerhayes, Jr. |
| 3,019,346 | 1/1962 | Laycak |
| 3,439,988 | 4/1969 | Breske ............................ 356/237 |
| 3,590,258 | 6/1971 | Shibata .......................... 356/237 |
| 3,666,370 | 5/1972 | Seasholtz ....................... 356/237 |
| 3,734,626 | 5/1973 | Roberts et al. |
| 3,794,427 | 2/1974 | Shibata et al. ................ 356/237 |
| 3,797,943 | 3/1974 | Nagao et al. .................. 356/237 |
| 3,814,945 | 6/1974 | Allnutt et al. ................. 250/571 |
| 3,857,637 | 12/1974 | Obenreder .................... 356/237 |
| 3,866,038 | 2/1975 | Korth ............................ 250/563 |
| 3,871,771 | 3/1975 | Scott |
| 3,892,494 | 7/1975 | Baker et al. .................. 356/237 |
| 3,976,382 | 8/1976 | Westby ......................... 356/237 |
| 4,130,361 | 12/1978 | Humphrey ................... 356/125 |
| 4,172,666 | 10/1979 | Clark ........................... 356/431 |
| 4,207,467 | 6/1980 | Doyle ........................... 356/382 |

FOREIGN PATENT DOCUMENTS

| | | |
|---|---|---|
| 2439988 | 8/1976 | Fed. Rep. of Germany. |
| WO84/02398 | 12/1983 | PCT Int'l Appl. |
| 2095398 | 9/1982 | United Kingdom. |
| 2117897 | 10/1983 | United Kingdom. |
| 2118304 | 10/1983 | United Kingdom. |

Primary Examiner—Vincent P. McGraw
Attorney, Agent, or Firm—Larson and Taylor

[57] ABSTRACT

This invention relates to electro-optical sensing of form type and other defects on surfaces such as sheet metal or plastic panels. Method and apparatus are disclosed for detection and quantification of defects such as dents, creases, low spots, flat spots, etc. which are a result of the manufacturing, material handling and assembly process. Surfaces of interest are generally those of automobile body panels, (e.g. hoods, fenders), refrigerator panels, furniture panels, and aircraft panels. Similar applications exist to dies and other formed metallic or plastic parts. Both automatic and human visual methods and apparatus are disclosed. The disclosed invention is also effective on paint defects such as orange peel encountered in automotive and other applications. Assemblies of panels, such as car bodies may also be inspected using the invention, and both fixed and moving (e.g. robotic) sensor versions are disclosed.

58 Claims, 35 Drawing Figures

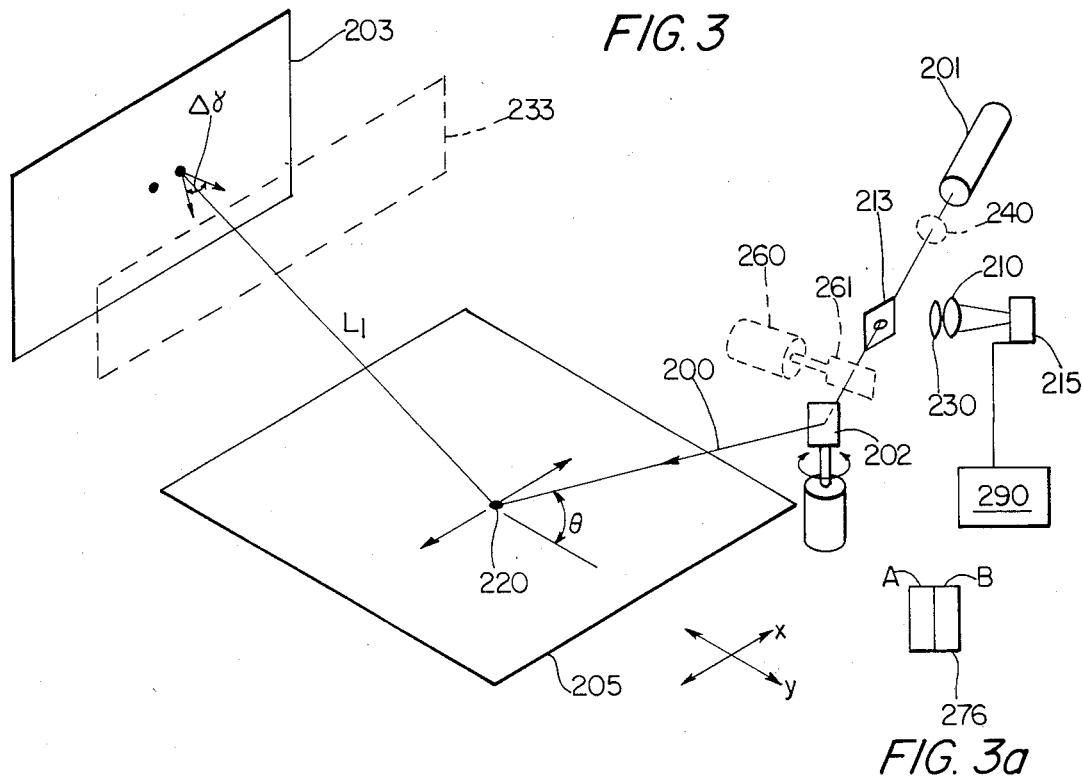
FIG. 3
FIG. 3a
NORMAL SURFACE ──────────────
SURFACE WITH ──────────⌐⌐──────
DENT
FIG. 3'
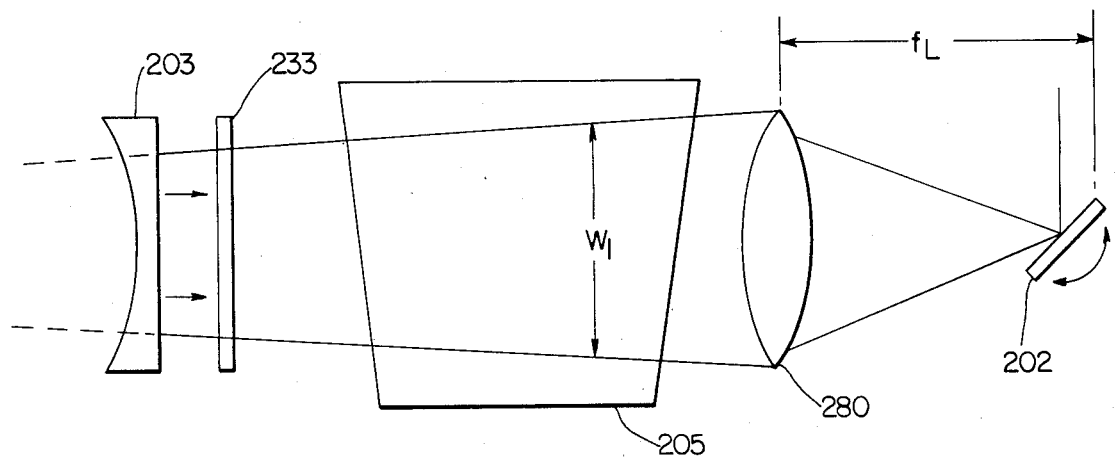
FIG. 3f

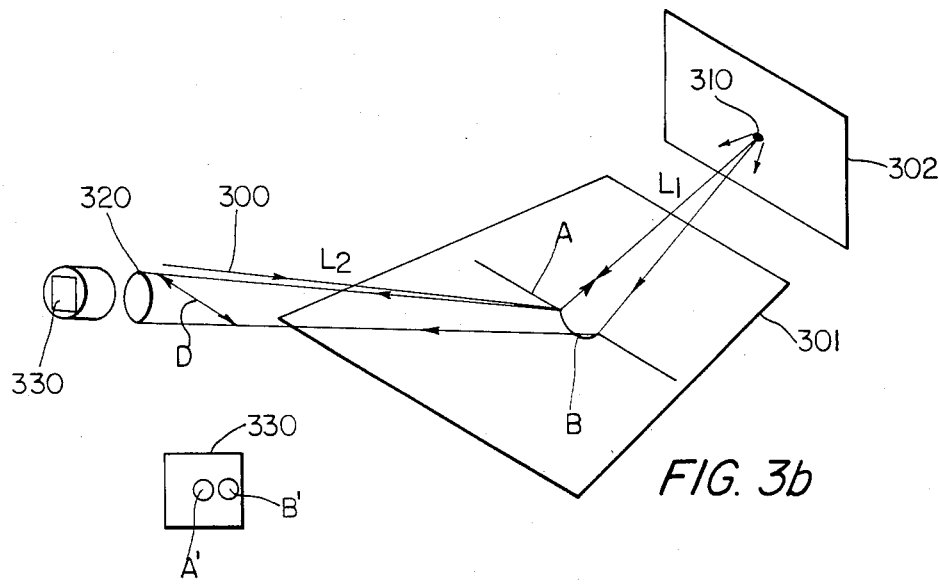
FIG. 3b
FIG. 3c
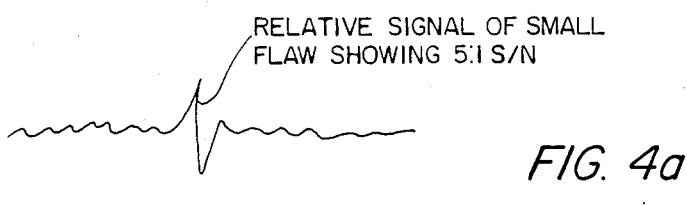
FIG. 4a
FIG. 4b
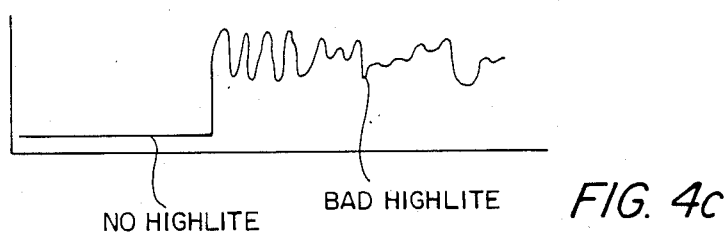
FIG. 4c
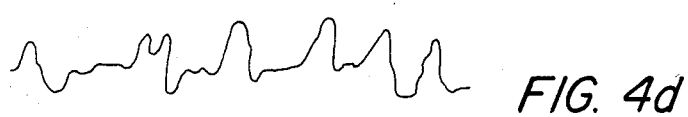
FIG. 4d

| RATING | SEVERITY | WIDTH |
|--------|----------|-------|
| XXXX   | 42       | 12    |
| XXX    | 31       | 6     |
| X      | 10       | 2     |

RATING DERIVED FROM PRODUCT OF FLAW SEVERITY X WIDTH.

FLAWS SHOWN ON SIMULATED HOOD. PLAN VIEW IN APPROXIMATE LOCATION.

COMPUTER PRESENTATION OF DEFECTS ON AN AUTOMOBILE HOOD.

PANEL SURFACE FLAW INSPECTION

BACKGROUND OF THE INVENTION

Sheet metal panels formed by a stamping process, plastic or non-metallic panels formed by injection molding and other similar parts often show dents, low spots and other geometric distortions from irregularities in the dies or molds used to manufacture the part or from handling damage. These may manifest themselves as indents, outdents, creases, buckles, spring back, high spots, low spots, dish shapes, tears and a myriad of other similar defects which must be detected in the inspection process. Such inspection is generally done before painting or plating the parts, that is before a significant amount of additional money is spent on the part or its assembly. However, subsequent handling and the assembly (e.g. welding) or paint processes themselves also can impart damage, requiring reinspection.

Such panels are often inspected visually in an environment of florescent linear lighting which assists the inspector to determine the quality of the panel by observing distortions in the reflected image of the lights. However, the florescent lights are of relatively low contrast and in any case, such inspection is slow and subjective. It is therefore very desirable to have a method for rapidly, automatically and objectively evaluating such defects (both for audit and 100% inspection purposes). Such rapid, quantitative analysis of defects is important for control of processes to achieve uniform flow of quality product in just-in-time production systems and to achieve uniform acceptance standards between vendors and customers.

There are numerous optical methods to measure the contour of the part that could in theory discriminate such flaws, triangulation or light sectioning for example. Another technique along with imaging a grill or grid of lines through the panel was described in the article by Lippincott and Stark, Aug. 15, 1982, *Applied Optics*. A similar electro-optical sensor actually constructed for inspection of body panel flaws was described in U.S. Pat. No. 4,394,683 by two of the inventors and their colleagues, which patent is incorporated herein by reference. This uses deviation of grid lines imaged through the panel and a varient is described in FIG. 13 of this patent. This works reasonably well but signal to noise levels are often low, especially on poorly highlighted panels. In addition, relatively low angles of incidence to panels are necessitated which makes operation difficult in many cases.

SUMMARY OF THE INVENTION

Described herein therefore are embodiments of the invention which obviate much of the signal to noise, light power and other difficulties obtained with grid or line image deviation systems and furthermore facilitate sensor to part positioning with no critical focal depths or the like. This then facilitates in-line or robotically controlled machines which do not require the surface inspected to be in a closely controlled position.

While primarily aimed at sheet metal and plastic panels (e.g. hoods, fenders, doors, etc.), it is also useful on assemblies of such panels as in car bodies. The invention checks the panel for manufacturing and handling flaws and those types of defects which are inherent to plastic molding processes such as waves and sinks which occur in the manufacture of plastic panels.

BRIEF DESCRIPTION OF THE DRAWINGS

This invention is illustrated in the following embodiments:

FIG. 3 illustrates a retroreflection, scanned beam, embodiment of the invention.

FIG. 3' depicts two characteristic signals received on the screen depicted in FIG. 3.

FIG. 3a schematically depicts a split detector for detecting the beam in FIG. 3.

FIG. 3b depicts another embodiment of the invention using a scanned beam and retroreflector.

FIG. 3c schematically depicts a split detector for detecting the beam in FIG. 3b.

FIG. 3f schematically depicts a collimated beam modification for the embodiment depicted in FIG. 3.

FIGS. 4a to 4d illustrate effects of various surface conditions.

FIG. 6b illustrates a glasses embodiment of the point source depicted in FIG. 6a.

DETAILED DESCRIPTION OF THE PREFERRED EMBODIMENTS

The invention is broadly described as follows:

1. A method for inspecting surfaces comprising the steps of;
   illuminating said surface with light, with a retroreflective material returning light reflected from said surface such that it is re-reflected from said surface,
   detecting said re-reflected light, and
   determining from said detected re-reflected light any defects in said surface.

2. A method of detection of defects in a surface comprising the steps of;
   scanning a spot or other zone of light across a screen,
   imaging said zone of light on said screen, reflected via said surface, onto an image position sensing detector,
   determining, from changes in the position of said zone image as said beam is swept across said screen, any defects in said surface.

3. A method of detection of defects on a surface comprising the steps of;
   providing at least one illuminated line, imaging said illuminated line by reflection from said surface onto a photodetector, analyzing the signals from said photodetector to determine deviations in the position of said image of said illuminated line across a portion of said surface, and determining from said deviations, if any, any defects in said surface.

In addition, disclosed is apparatus to make visible form defects in surfaces comprising at least one light source means to illuminate said surface and retroreflective material means to redirect light reflected from said surface such that the rereflected light from said surface can be visually observed.

Apparatus is also disclosed to reduce the embodiments of the invention in a practical manner.

Figure 1:
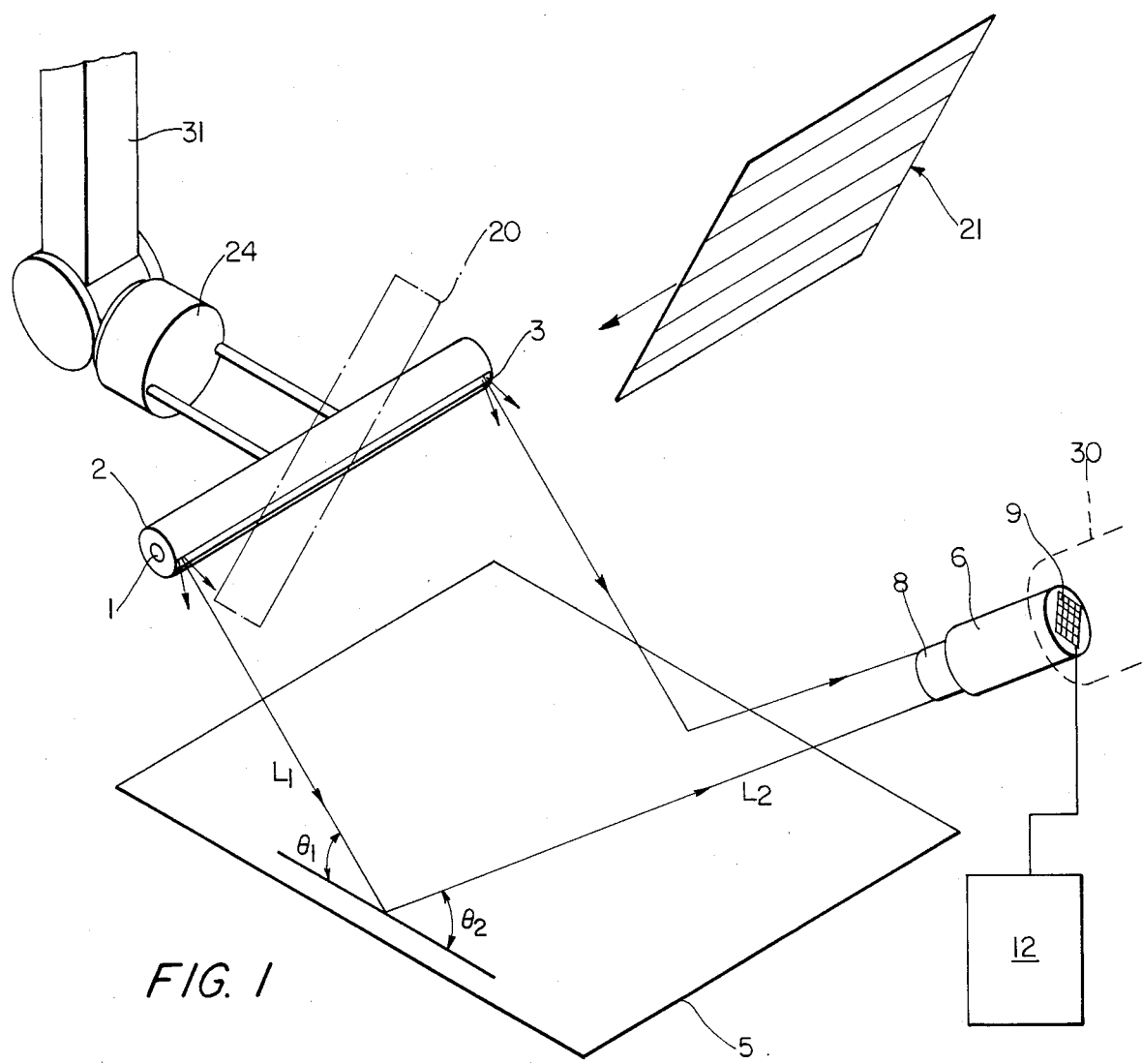
FIG. 1 illustrates a line or grid image deviation embodiment of the invention.

An embodiment of the line image scan type is shown in FIG. 1. A grid or line section, the latter being shown, is placed horizontal to the surface of the panel and deviations of portions of the line are read as the sensor is moved relative to the panel defects. This system can employ a scanning mirror or a robot to move the sensor back and forth, or the panel can move under the sensor as well.

In this case a linear lamp 1 enclosed in housing 2 having a slit opening 3 is used as an illumination line or slit source for a surface of a panel 5 to be examined (e.g. a sheet metal car hood or door). The slit source is viewed by solid state TV camera 6 containing a lens 8 and a photo detector unit, e.g. matrix diode array 9, connected to a processing unit 12. A suitable array is a GE TN2500.

Figure 1A:
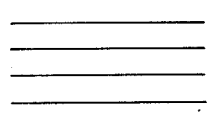
FIGS. 1a, 1b, 1c and 1d illustrate various line images.
Figure 1B:
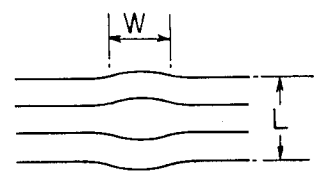

On a good panel, the deviation of points on any one line image and indeed between successive lines as the panel is scanned relative to the sensor is small in any local zone except in areas where contour lines or other known features of the panel exist. The scan of a good panel is shown in FIG. 1a. However, when a low spot, ding, dimple or what have you appears, the lines distort as is shown in FIG. 1b. This distortion can be characterized by determining slopes or positioned changes of the deviated line image. Defect parameters are put on as a function of the slope of the panel distortion, and/or its width, lengths, etc. Such defect indications can be obtained from the width "w" of the distorted lines or the change of frequency of the lines, or the like.

In this particular mode, it is very convenient to move the panel underneath the sensor (comprising the line source and detector) or conversely to move the sensor over the panel. For example, if the sensor is attached to a robot, it can be programmably scanned over panels. In the robot program, one can ignore certain sections such as where contour lines exist, at the edges of the panel, etc.

Figure 1C:
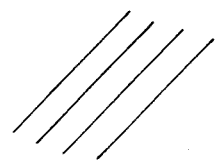
Figure 1D:

As shown in FIG. 1, there are some other aspects to this embodiment. First of all, the line need not be horizontal, i.e. parallel to the panel as shown but could be projected at an angle as by lamp 20 (shown in phantom). The 45° projection shown in phantom makes an excellent choice in many cases. Indeed in some cases, it is desirable to rotate the line over a sequence of angles (e.g. 0°–60°), for example to the new positon of lamp 20 in order to obtain the best result. For example, the rotated line image version as shown in FIG. 1 has a sharp discontinuity that is made much much more visible on certain types of flaws when the line (or grid, see below) is angled to the panel (i.e. not at a zero angle parallel to the surface). The good panel scan using a rotated line is shown in FIG. 1c while a flaw detected scan is shown in FIG. 1d.

The line can also be perpendicular to the surface (90°). In this case, sensitivity is least but contrast is best. To cover an area, a grid of lines is required.

Because of the different angles of view at which flaws appear best, and in fact one can be looking across a panel or lengthwise on a panel and obtain different impressions of a defect depending on just what its form is, it is often desirable to program the robot to come at the panel from different approach angles. For example, the robot could look first along the panel length, then across its width, at 45° or anything else that tends to make certain defects visible. It is characteristic of many stamping defects that certain types always occur in certain places on a particular panel due to die error, etc. Thus, one can program only to look in these areas or at different view angles depending on what flaw it is.

Because of the relationship between the distances L1 and L2 of the light source and of the camera to the panel, respectively, it is desirable in some cases to have this distance programmable. In this case, separate robot arms such as robot arm 31 holding the light source and robot arm 30 holding a camera can be individually programmed to vary the angles of incidence, $\theta 1$ and $\theta 2$ as well as the distances L1 and L2 from the panel. Generally speaking, the larger L1 and L2 are, the more resolution is obtained but the contrast of the defect drops (especially true for L1). Therefore, very large distances are effective only when a smooth highlighted surface is available, as on good painted panels, well highlighted (oiled) metal panels, etc. Small angles $\theta$ also help create a smooth surface view, but cause a reduction in sensitivity. At extreme angles (e.g. $\theta$ under 5°) contrast is sufficient even on raw metal panels if L1 is short, but operation is difficult.

It should be noted that a single line is quite usefel but requires a mechanical scan of the sensor relative to the panel to map out the complete panel. This could be done by moving the panel, the sensor units, or both.

Alternatively or additionally, however, a grille of parallel lines (e.g. grille 21) or a grid of crossed lines can be employed in place of a single line. In this case, one can obtain the reading simultaneously using the 2 axis scanning capabilities of the TV camera. However, the lighting angles and the like are not quite as good from the multiple grid locations as they could be from a single angle of incidence from the surface and indeed the total optical system can be enchanced for the single line more than it can for the grid or grille.

Basic problems, if any, with this FIG. 1 embodiment are the relative lack of contrast on poorly oiled panels and the requirement to utilize relatively low angles of incidence in order to get good useable contrast, i.e. $\theta$ in the range of 30 degrees or less. This makes a more difficult scanning requirement given the different types of slopes in panels. It is also generally desired to have light incident more normal (e.g. $\theta > 50°$) to the panel to facilitate the programming of the system as well as to keep the sensor package small such that one might be able to utilize the light source and detector unit in the same package.

It is clear that for use of the single line above, one needs to store in memory the individual line description and compare it sequentially with other lines. A similar system has been disclosed in a recent copending patent application by the inventors relative to contrast based (as opposed to geometric based as herein) surface flaw detection, including systems for doing so in real time which is necessary for high speed parts inspection (U.S. Ser. No. 525,801). U.S. Pat. No. 4,305,661 is also a reference for flaw detection of this type as well as along a single scan line.

In the present system, as in the other system disclosed above in U.S. Pat. No. 4,394,683, surface preparation on raw sheet metal panels is generally required using coatings such as highlighted oil applied onto the surface (or other surface conditioning) such that the surface appears suitably reflective. In-line this is best done in such a way that the ripples in the oil, if any, remain parallel in the direction of scan. A system of this type for in-line has been shown in U.S. Pat. No. 4,394,683 in FIG. 13.

Note that a programmable rotation motor 24 can be utilized to rotate the line grid, or grille light source into the positon of lamp 20 in a programmable way such that movement is linked to the inspections by the camera which then looks for maximum defect indication. For example, on a certain defect viewed with line angles of 30°, a maximum line distortion might be indicated. This angle of maximum effect can also be used to describe the defect too. Different types of defects have different angles of maximum effect in any one view.

There are several other inspection rationales relative to this system and those described in subsequent embodiments. For example, on most panels one knows where the defects can exist. Therefore, one can go immediately to those areas and look with the most effort, perhaps approaching the panel from different directions at different angles relative to the panel length axis at different standoffs L1 and/or L2 and with different grid rotational positions. Any or all of these and other parameters can be varied to suit the task at hand.

It is also contemplated that one can have different types of lines and grids interchangeably on a turret which can be interchanged with a single light source or with multiple light sources. This allows grids or grilles at different angles and spacings to be repetatively viewed and the best description of panel defects obtained.

Another embodiment of the invention replaces, in essence, the line source of FIG. 1 with a single point laser scan. This occurs in two modes. In the first mode, shown in FIG. 2, a point 100 produced by a laser 102 and a rotating mirror 103 is sequentially swept across a ground glass screen 110. This creates in time sequence the "line" of FIG. 1. Each point on that screen is then imaged sequentially onto a TV camera 130 viewing the screen through reflection off of a panel 131. In place of TV camera 130, one can use a synchronizing mirror scan (not shown) maintaining the point 100 image on a linear diode array (or an analog positon sensing detector such as a UDT Pin 2D or SC10—the analog sensors provide often more speed or range). A CRT has also been used to generate a flying spot which worked well but intensity is weak unless highly sensitive detectors are used.

While mainly of use on geometric distortions of the panels, it is clear that the camera of such a system can be used to see scratches and other sharper deformities of the panel as well using the same light source or additional supplementary light sources to illuminate the panel surface.

Where a grid or grille is desired such as shown by grille 21 in FIG. 1, it is also possible to have a scanning unit mounted on a robot such that the robot only has to place the sensor unit in various fixed positions relative to the panel. This makes it easier to program the robot since it does not have to make sweeps in a uniform manner.

However, even a sweep of a line across the panel over let's say a four inch zone can be provided by the end of an arm tooling having a separate sweep scan on it. One can also use a mirror type system to sweep this back and forth on the surface of the part. These possibilities are described relative to the analogous cases in the embodiments described below.

A two axis analog point (spot) image position detector such as a UDT SC10 can also be used in place of a raster scan TV sensor 130 to obtain a much higher frequency response (e.g. 2 KHz) than the relatively limited 30 scans/sec of a conventional TV. High speed TV cameras at 400 scans/sec can also be used as can random axis TV scans such as advanced forms of the GE CID (solid state) cameras which allow only the zone where the point exists to be scanned.

A version using a synchronized scan with a linear diode array is capable of 1000 array scans and therefore 1000 data points/sec. Using 200 data points across a 10" panel strip, this represents 0.050" width per point which is capable of resolving most geometric defects of interest. At 7000 scans/sec, this is 5 sweeps/sec. across the 10" panel strip. Actually, 0.1" spot image zones are often sufficient, giving 10 sweeps/sec. This allows a forward scan speed of at least one inch/sec., but ofter higher scan speeds are possible as 100% coverage is not required to detect geometric form flaws which are usually much larger in their effect than 0.1". Thus, a scan rate of 5 inches/sec. is typically possible.

In practicing the above embodiment, however, a more advantageous version was found which was totally unexpected. A sheet of retroreflective material was used as the light "source". A laser (or other) beam was scanned from the same side as the image sensor such that the scanned beam was returned by retroreflection to the image sensor. While bearing similarity to FIG. 2, this functions much better and needs some explanation.

Figures 3D, 3E:
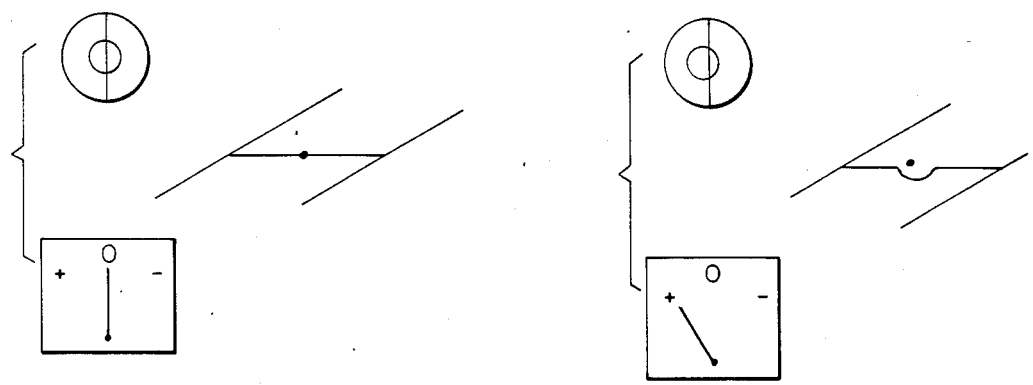
FIGS. 3d and 3e schematically depict a beam scan across a surface without and with a defect, and the spot position received on a bi-cell detector and the output produced thereby.

Considering now the embodiment depicted in FIG. 3, a substantially collimated "beam" of light 200 from a laser 201 is directed by means of a scanning mirror 202 to a retroreflective sheet 203 by first bouncing it off the test panel 205 in question. Two typical scans which are reflected from the panel to the screen are shown in FIG. 3'. The oppositely angled slopes at the dent are caused by the slope on one side of the dent which is opposite to the slope on the other side of the dent. Because the retroreflecting material is not perfect, not all of the light returns along the same path. Instead some of the light returns over a range of solid angles that spreads a small amount relative to the input beam. A lens 210 images the "cone" of returning light from the retroreflecting object material via a mirror (having a hole for initial beam transmission through it) or beam splitter 213. An image position detector 215 senses variations in the 'spot' shaped image position which is indicative of a local perturbation 220 in the panel 205. Note that the laser makes an excellent source allowing high speed scans, but the invention will function with non-laser sources.

The image positon detector can be a split or bicell detector (e.g. UDT Corporation Pin 2D), a single axis continuous detector such as a UDT LC5, a two axis continuous detector such as a UDT SC10, a discrete detector with a mask, a linear diode array, a two dimensional diode array, or a TV camera, for example.

In order to consider a larger area of the panel, the beam can be raster scanned with another scanning mirror to scan perpendicular to the sweep direction.

"Noise" in the form of light scattered by the surface and reflected directly back from the panel (i.e. not passing to and from the retroreflector material) can be eliminated (as is highly desirable for best results) by using a polarized laser beam and a polarizer 230 which is "crossed" (i.e. 90°) to the incident beam polarization blocking the polarized direct reflection from the panel. An appropriate (e.g. ¼ wave) retardation plate 233 will permit the light returning from the retroreflector and the panel to pass this polarizer (as it is rotated 90° after passing through twice). Such objectionable reflection is worse on white or light colored painted panels and highlighted unpainted panels. (Signals can be up to 3 times, for example, the retroreflected levels.) It is minimal on black or dark painted panels. Other polarizer retardation arrangements are possible to accomplish the same goals.

Another means to remove the direct reflection includes sensing the direct reflection using a second detector (not shown) slightly off axis from the beam splitter 213 and subtracting that signal from the spot position sensor output.

The transit time difference from direct reflection from the panel as opposed to light that is returning from the retroreflector path can also be used to differentiate this noise signal but this is extremely difficult due to the short time interval represented (a few nano seconds).

An additional advantage of this embodiment of the invention is that the light coming from the retroreflector returns on approximately the same path as the incident beam. A very high power utilization results, and a bad surface then will deflect this beam so that the electronics is just looking for a local change in position due to local form errors (e.g. a flat spot on a curved surface, or a curved depression on a quasi-flat surface). If a split detector 216 (e.g. UDT Pin 2D), having two elements A and B as shown in FIG. 3a, is sensing the position of the beam, then it is the difference A minus B which gives the information. The difference A minus B divided by the sum A plus B gives a normalized output. This tolerates a wider variation of part reflectivity without causing difficulty with the signal. The sum A+B is the returned light intensity proportional to the reflectivity of the panel.

FIG. 3b illustrates another embodiment of the invention. In this embodiment, a light beam 300 is reflected from the normal surface of the panel 301, reaches reflective screen 302 producing a zone 310 (e.g. a spot), and is re-emitted. Lens 320, with aperture width D, can image the spot on the screen over all areas of the surface within its field of view which subtends a zone of the surface considerably larger than the incident beam.

For example, if the beam is directed at the screen via the normal surface portion A, one can image from the normal surface the spot on the screen which includes a portion from the sloped area of a large dent B.

There are then two images, A' and B', formed on the detector 330 as shown in FIG. 3c. For more moderate slopes, the two images come together to form a blurred image which "grows" in one direction or the other as the beam is scanned over the sloped sides of the dent. The direction of shift is opposite depending on slope direction—up dents being reverse of down dents for any given scan direction. This is illustrated in FIGS. 5a-5e, where it is also noticed that the maximum signal amplitude from the analog spot position detector corresponds to the maximum slope of the part surface. Since both positive and negative slopes occur in scanning across a dent for example, the signal can go plus to minus.

In the center of the dent, the image can grow in both directions (at some point resulting in no centroid shift). Thus, the image of the spot on the screen can be formed through the undisturbed portion of the surface adjacent the dent plus both oppositely sloped sides of the dent.

Especially for large beam sizes (e.g. 0.5 cm), the beam itself can break up as it crosses the dent causing 2 beams (or even 3) to appear on the screen. This can result in more image formation.

The above function is, however, modified by the action of the retroreflective material chosen for the screen 302. Such material is very directional in its nature reflecting only a small angular cone (typically) of light around the axis of the beam on its surface.

Light can only be imaged from surface zones illuminated by the light returning from the retroreflector, i.e. returning from a small cone or other angular zone of light about the incident beam direction or axis taken to the retroreflector. For example, at $L1=2$ meters, such a cone at the lens aperture is typically 30 mm in diameter where a high quality glass bead retroreflective material is used.

Since the retroreflector is needed to allow useable light levels to be attained at the photodetector or human eye, this then means that only imaging of spots on the screen can be made over small angular zones. For large dents, the surface slope can thus direct the re-reflected light completely off the lens for $L2$ large and/or $D$ small. For this reason, it is preferable to have $D$ as large as possible for any given choice of $L2$.

Indeed, one can use no lens at all but just large detectors to one side or the other of the incident beam axis to detect the shift in position of the re-reflected cone of light from the retroreflective material.

Where a lens is used, it is desirable to make the object distance equal $L1+L2$ especially if one is to separate the undesired direct back reflected light from that returning via the retroreflector. However, one can operate over a wide range of object distances and still obtain good results.

As noted earlier, the returning angle of light from the retroreflector can be somewhat larger than the outgoing beam. This is due to characteristics of the retroreflector itself, i.e. it is not a perfect retroreflector but a retroreflecting screen composed of myriads of minute elements (usually glass beads). Furthermore, the panel (die, model, etc.) surface itself is not a perfect mirror in which case it has somewhat spread the light from its surface anyway. Thus the 'spot' on the detector is formed by viewing through a larger area of panel surface than the reflector. Where variations occur locally between this larger area and the instantaneous surface deflecting the beam, spot distortions or spot movements occur.

Lens aperture can accept light returning over larger angular zones than the incident beam and this allows the detector to view image zones of the retroreflective material through the surface from an axis. In other words, one is now looking at the retroreflector not directly along the beam path but slightly displaced from it—which works as long as the angular displacement is a few degrees or less, i.e. within the return cone of the retroreflector.

For example, if one scans across a section of surface of the part with no local slope distortion, the image on the bicell detector is symetrical. This example is depicted schematically in FIG. 3d. If, however, there is such a distortion with the slope as let us say locally first downward (i.e. a down ding) and the beam hits it, it is deflected to the retroreflector and displaced from its original position. This example is depicted schematically in FIG. 3e. This is picked up as a direct displacement since the detector unit is essentially viewing the surface from behind, i.e. through the actual unsloped portion of the surface. In other words, we have created a local reference system wherein the "normal" surface near the defect is used as a reference (geometric in this case) against the deviated surface. This is indicative of the signals seen.

Clearly, as it goes to the other side, the reverse occurs. We are viewing the surface through the sloped area but the beam is now bouncing off the normal surface. It should be noted that we can shift detector axis position above or below the defect as well causing the detector to see in a different way the defects that are scanned across various slopes.

In short, it is the distortion or shifting of the image of the beam spot on the detector, due to the centroid shift created by an averaging around the instantaneous points hit by the incident beam and the comparison of those points to other points either in advance or behind, above or below the instantaneous point, that causes the essential change in position data that creates the signal. These various parameters can be adjusted to provide the best results for any types of panels, defects, etc.

All of the above works as long as the panel is relatively reflective, such as painted panels or panels which have been highlighted (that is coated with a light, free flowing oil film typically kerosene based). Any other wetting type film that makes it appear mirror-like would be suitable as well. Indeed, heavier oils such as WD-40 have been used successfully. The retroreflective embodiments can operate at much higher angles of incidence than the embodiments shown in FIGS. 1 or 2 and still give good signal to noise, the noise being determined by the roughness of the surface, the oil film, etc. This is of use in utilizing a robotic positioning system as shown below.

The flaw itself can be characterized by looking at this normalized signal (and/or a processed version thereof to remove both DC and/or high frequency, e.g. highlighted or paint ripple) and evaluating the width of the flaw and its amplitude in a given scan and also the extent of this flaw as measured in the scanning direction. Indents and outdents are also normally identifiable (see FIG. 5 below).

It is noted that reflective defects, i.e. a dark spot on a light surface or a dull paint or highlight job, desirably show up as surface light reflectivity variations, not as shifts in image position. Accordingly, these conditions can be differentiated from true defect conditions.

Typical values used in an extremely successful working example of the above embodiment are:
mirror sweep rate, 60 sweep/sec. forward and backward, effectively 120/sec.;
general Scanning Corp. mirror oscillator with 2" square mirror;
width of beam on panel 0.2 inches (0.5 cm);
laser, 2 mw HeNe polarized, Coherent Model CR90-21HP;
retroreflective material, 3M Scotchlight using glass beads;
imaging lens 75 mm, F1.4;
detector, UDT Corp. PIN 2D;
angle of incidence to and reflection from panel 60°;
distance to panel L1=L2=3 ft. (0.9 m).

It is noted that with this large beam size, the unit even operates on overly thick highlight oil conditions (e.g. WD-40) that have excessive streaking. It is further noted that best results occur for large lens apertures which can collect the maximum amount and spread of returned light.

Figure 2:
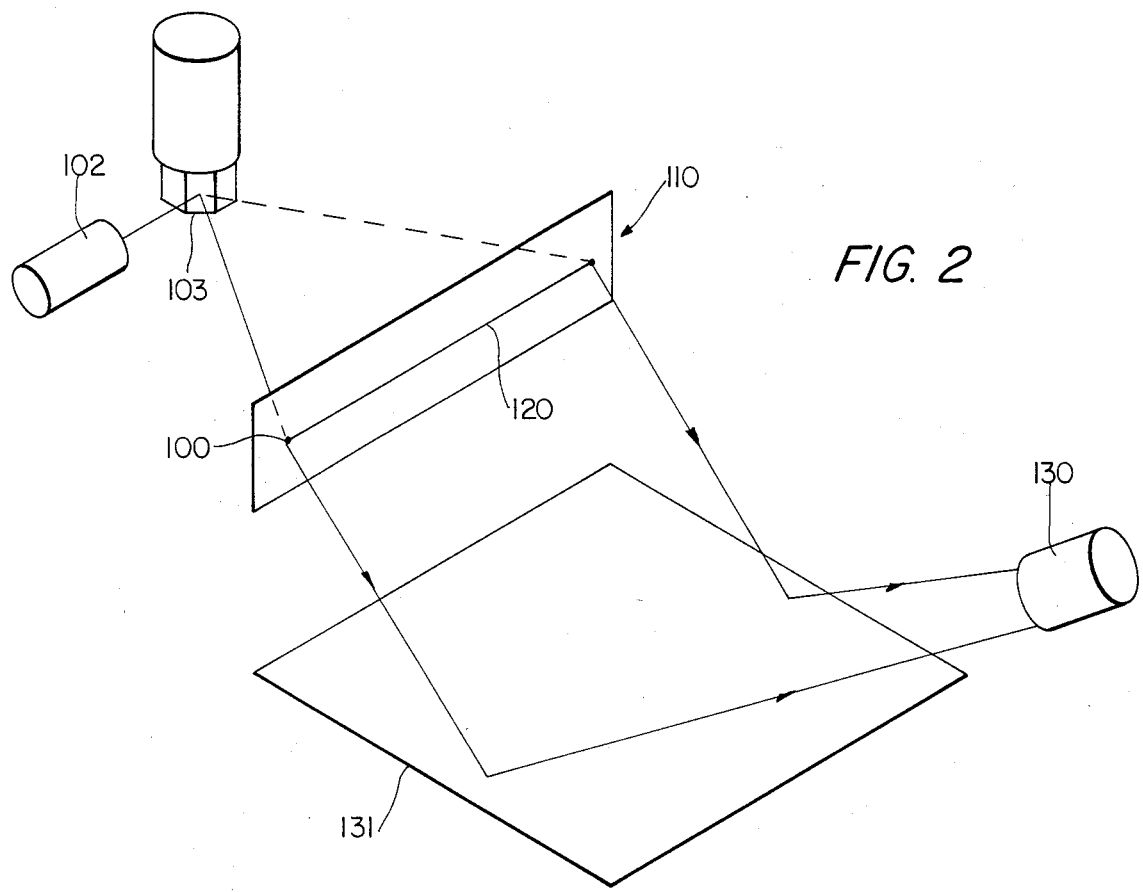
FIG. 2 illustrates a swept point scan embodiment of the invention.

The previous embodiment of FIG. 2 essentially images a point on a ground glass or other screen through the surface of the panel onto the image detector unit. Clearly, if the surface of the panel had a slope to it, it would throw the light off at another angle resulting in an image spot shift on the detector.

In the FIG. 3 embodiment of the retroreflector with the light source on the same side as the detector, the light impacts a point of the panel and ostensibly comes back from the retroreflector along the same path. Therefore, one still gets nearly full light power back—a big plus and a huge signal improvement over the FIG. 2 apparatus which loses most of the light generated.

However, on the face of it, one would think that the return beam would not move since it would seemingly follow the same path on its return as outgoing to the retroreflector. In fact, however, it does move, and in a very pronounced way. This is because the retroreflective screen which essentially re-emits with a large number of small emitters, is broader in its re-emission angle than the angle of light projection through the panel. Therefore an image can be formed using areas of the surface not directly illuminated and one can get a localized comparison of the instantaneous spot to the area around the instantaneous spot including a sloped surface of the panel. One can also compare a trailing or leading area of the panel to the instantaneous point, or an area offset higher or lower as well simply by changing the placement of the sensor viewing axis relative to the output beam axis. In fact, one can use multiple detectors each comparing to a different zone and compare those.

The orientation of the retroreflecting material to the incident beam is preferably normal to it, but neither this angle or the material position is particularly important—a big advantage for practical use on complex contoured panels with robots, etc. (It is much better than the FIG. 1 or FIG. 2 apparatus in this regard.) However, the sensitivity of the panel defect detection is dependent on the distance L1 of the retroreflective material (e.g. Scotchlite by 3M Company) away from the panel, the distance L2 to the sensor, as well as the incidence angle $\theta$ to the panel. The farther away or the larger (i.e. more normal) $\theta$, the more sensitivity to panel geometric distortions.

The panel in question or the total inspection areas can be surrounded by the retroreflective material such that it can accommodate reflection from various panel types and slopes of the panel itself. Alternatively, the retroreflective material can be carried with the sensor portion, attached to the same member or moved in concert (e.g. by a second robot).

A major advantage of this invention is that the sensor, including the laser (or other light generating means) can be held less rigidly or indeed carried by a continuously moving robot as the retroreflector keeps the light on the optical path for most orientations. Indeed, the retroreflector itself can be tilted substantially relative to the panel surface and still keep the light returning on its optical path. This is of crutial importance as many panels have substantial curvature causing reflections to be directed at numerous (compound) angles as one scans. This makes the invention extremely practical in its implementation.

Another advantage is that a sensor can be constructed to project and receive light close to normal incidence (i.e. perpendicular) to the panel surface implying that the sensor package itself can be small and light and easily carried by a robot if necessary. In order to facilitate this, the retroreflecting material must surround the inspection area and be located at all angles necessary to accommodate the various reflections off the surface. A working system operating at $\theta = 70°$ has been constructed.

Another advantage is that analog spot position detectors such as bicell detectors (e.g. UDZT Pin 2D) are very fast, low in cost, and have low noise so that inspection time can be fast. Differential measurement of two detector elements sensing the positon of the imaged spot of light give the necessary information assuming the spot does not move too much off one detector element. When the output is divided by the sum of the detector outputs, the sensor is normalized and less sensitive to general reflectivities of the panels which can change with color, oil film, etc. Such normalization can also be accomplished with continuous analog sensors such as UDT SC-10, PIN 5D, LC10 etc.

Another advantage is that this system will work on panels which are painted or unpainted. In the latter case, the unpainted panels are sprayed, wiped or otherwise lightly coated with an oil film to smooth over the natural surface roughness of the surface itself. It is preferred to wipe the oil film in a direction parallel to the lateral scan direction so that the scan does not cross the ripples in the oil (which are geometric in nature and can appear as "defects" or increase greatly the background noise level). On plastic panels, the natural surface finish is often high enough to require no oil coating, at least at lower incidence angles.

Using illumination angles closer to the grazing angles will make the surface appear to look smoother which allows one to work with rougher surfaces. However, it also can produce less sensitivity to defects, depending on the defect type in question. This invention will operate on plastic panels (e.g. RIM, SMC) without oil, but require angles generally under 45°.

Another embodiment of the invention modifying FIG. 3 is shown in FIG. 3f. In this case, a collimated or converged beam using a cylinder lens 280 is shown. (A long focal length spherical lens can also be used, as can a cylindrical or spherical mirror.) This allows the package to be folded around while still maintaining a good sized beam sweep (e.g. 10") on the surface and while limiting the size of the quarter wave material required. This is occasioned by the fact that quarter wave material is difficult to obtain in sizes larger than 12 inches. This also makes it possible to have a smaller width retroreflector and therefore can desirably reduce the size of the unit. (With no lens, such as lens 280, the reflected beam from a convex curved surface typical of an outer automative body panel, such as a fender, diverges, requiring a larger expanse of retroreflective material than the beam sweep width would indicate. This causes excessive sensor package size.)

As shown, a large lens 280 (or for that matter curved mirror) is placed such that the scanning mirror 202 is approximately at its focal length $f_L$. This collimates, or as shown, slightly converges the swept beam onto the surface of the part in one direction. The lens 280 is preferably a cylinder lens but can be a spherical lens of a long focal length (which effectively acts like a cylinder lens over its central portion covered by the beam and does not do much to the beam shape itself other than slightly focus it which is okay if not too finely focused on the part surface).

The beam then hits the surface of the panel, and goes through the quarter wave material 233 which now can be located at the retroreflector 203 while still allowing a full 12" swath, $W_1$ say. It is noted that if this is not used to obtain a 12 inch swath with a limited 12 inch retroreflector piece, one has to locate it near the surface of the panel which can create a difficult constructional problem.

When, as shown, the beam sweep is converged to the retroreflector, if the lens then is placed near the panel, the actual sweep $W_1$, on the panel can be, let us say, 16 inches while still preserving a 12 inch retroreflector and quarter wave material.

The beam path can also be folded in order to make an easily manageable sensor unit which can be utilized on the end of robots or stacked side by side without undue space requirements.

Note that when stacked side by side, a common sheet of retroreflective material and quarter wave material can be used if desired, with only the scan and detection units duplicated.

There are many additional points to mention. First of all, consider the question of highlight oil condition and paint finish. For example, consider FIGS. 4a to 4d which illustrate the signal of a single scan of the FIG. 3 apparatus across a panel with FIG. 4a showing good highlighting, FIG. 4b showing a relatively standard paint finish, or FIG. 4c showing two cases of bad highlighting where the oil has either not been applied or applied much too coarsely. A fifth example shown in FIG. 4d is that where the highlight oil is in streaks which are not running parallel to the direction of scan as in FIG. 4a but instead run perpendicular to the direction of scan causing the maximum distortion. This is, of course, to be avoided if possible. Plastic should also be scanned parallel to its "grain", if present (e.g. as on SMC).

First, some interesting things to point out. A well highlighted panel with the streaks of the highlight oil which had been rubbed on the panel running in a direction parallel to the scan actually looks better than some painted panels. Second, it is felt that since the sensor unit is seeing geometric distortions, the ripples in the painted panel can be considered to be the paint finish or in extreme cases "orange peel" and therefore the amplitude of the ripples can be used to analyze the quality of paint.

The third thing is clearly that when one gets a minimum ripple background surface on a highlighted panel, one knows that the correct amount of highlighting has been applied. Naturally, if a plastic panel or some other panel without requirements for highlighting is present, of course such highlighting is not required. For example, a plastic panel with no highlight is similar to FIG. 4a or FIG. 4b and sufficient for operation. Sometimes plastic can exhibit excess background noise (like FIG. 4d) due to a condition called "elephant hide" which is desirable to detect.

Clearly, however, when the magnitude of the ripples becomes too great, a poor (i.e. heavy, streaky) highlight paint finish or "elephant hide" condition can be signaled simply from the AC component of the detector signal during a sweep using known techniques. In some cases the component within a certain frequency and/or level band is chosen to represent the highlight oil (or paint finish) contribution.

A second determinant for improper conditions is when the signal amplitude is simply low, obviously indicative of poor reflective qualities of the surface as in the case of no highlight at all on a steel panel.

When used with highlighted panels, both of these conditions can be used to flag areas which can create invalid data due to highlight condition. Such "flags" can be fed to a computer to cause one or more things to occur:

1. The whole panel can be rejected and a re-look made after suitable highlighting.
2. The system can be used to help evaluate whether the highlight job is correct before making an analysis.
3. Particularly in 100% inspection in-line, the zone where the bad highlighting occurs can be blocked out of the computer memory and simply ignored so that the panel is not rejected for what probably is no problem with the actual surface, only the highlight. Indeed a special notation can be made such that the next panel is purposely inspected in this particular sector so that statistical data can still be built up. Naturally, if bad conditions could occur in this particular sector repeatedly in an in-line case (for example where an automatic highlight system is used such as shown in U.S. Pat. No. 4,394,683, FIG. 13, or otherwise) it can be then ascertained that something has gone wrong with the automatic highlighter as is clogged nozzles, broken brushes and the like and these conditions corrected.

FIGS. 5a to 5e illustrate signals of different flaws produced by the FIG. 3 apparatus. As can be seen, the type of dent in or out from the normal surface can be found from the signal direction. For the larger defects such as an approximately 5-10 cm wide low spot, the signal is spread out in the direction of scan. Knowledge of what magnitude, size and defect type(s) is present is invaluable in correcting process defects.

Figure 5A:
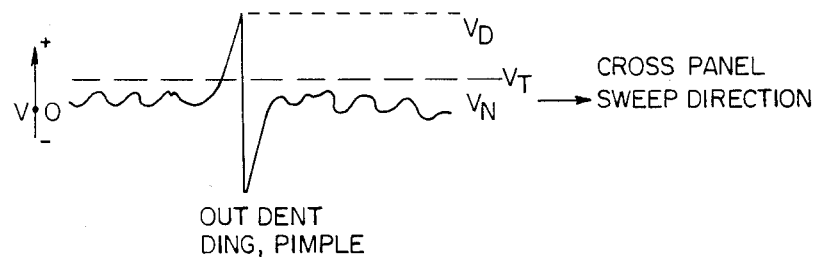
FIGS. 5a to 5e illustrate flaw signals of different types and their processing.

FIG. 5a also illustrates processing steps according to the invention. In the apparatus of FIG. 3, two signal processing steps are used. In the first, the signal is AC coupled to remove the DC frequency component of the surface. Next, the threshold $V_T$ is set above the maximum value $V_N$ max of the frequency components of background "noise". These components are indicative of the paint surface or the highlight surface surrounding the defect and, if excessive, can indicate an invalid signal reading in the area affected if the threshold is set at normal limits. Conversely, they can also be used to measure the quality of paint, finish or highlight. For example, the value of the average noise signal $V_{NA}$ gives an average value of the surface finish in the zone of interest. Orange peel ripple etc., can be detected when the signal exceeds some threshold $V_T$.

Figure 5B:
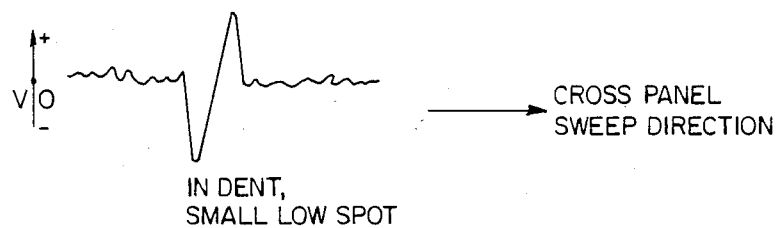

The image seems to have in FIG. 5a a positive going rise followed by a zero crossing and a negative portion. This is for an out ding. An in ding is the reverse (for a given scan direction) as shown in FIG. 5b.

In order to determine immediately the case at hand, there are two pieces of data, the height amplitude $V_D$ of the signal (with only those signals accepted above the background surface noise threshold $V_T$) and the width of the defect. The latter can be obtained from the trace or by looking at the number of successive scan lines where the defect appeared. Since this is for any one scan as we scan down a part, we can map out in essence the defects, by storing for each given scan the amount of defects shown in terms of a code as to where on the panel they appeared and coded to the type they are, the severity, and the width and/or length. In this way a table can be built up in the computer which can be printed out.

In a typical example on a black painted hood with the FIG. 3 apparatus, $V_A$ varied from 8 (small dirt in die) to 25 (severe dent) and $V_N$ was 2 illustrating the excellent signal to noise indication.

A variation is to take the derivative of the signal to obtain the rate of change of the slope of the part. This is easy to obtain as a signal and also gives a distinct output proportional to the severity of the defect.

Figure 5C:
Figure 5D:
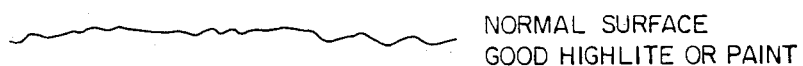
Figure 5E:
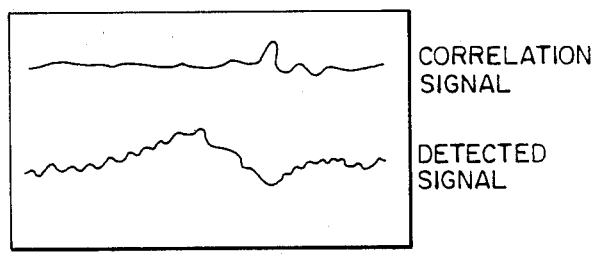

Other processing approaches are sometimes possible for large low spots, recoils etc. Shown in FIG. 5c is the signal from a defect which is wide but shallow and which does not provide the sharp second derivative signal.

One processing technique in this case is to correlate the characteristic curve produced to stored low spot signatures. A scope trace (FIG. 5e) shows the correlation peak (phase delayed) indicative of a typical low spot on the front of a hood. By tuning the frequency of the correlation, a maximum correlation signal for any low spot (or other defect) can be obtained. Since such tuning takes time, it can be desirable to identify such defects and come back to them, or to correlate such signals (in hardware or software) after the fact by storing them.

By using a longer illumination light source wavelength, into the infra red for example, one can eliminate the requirement for using a highlighting oil on the surface as the longer wavelength will not be as sensitive to the natural surface roughness of most materials of interest, e.g. steel, plastic, or aluminum. For example, at 10.6 $\mu$m ($CO_2$ laser wavelength) a steel panel looks 20 times smoother than it does at 6328 A (HeNe laser).

For example, consider that a waveguide $CO_2$ laser such as a 20 watt Laackman type could be utilized in the FIG. 3 drawing together with suitable IR retroreflective material (e.g. glass beads to 3 $\mu$m, machined metal at 10.6 $\mu$m; or in the FIG. 2 drawing with suitable dispersive material, such as IR "ground glass") and suitable infra red optics to form the image on a Pyroelectric Vidicon having a pair of adjacent IR detectors (arranged like 216), etc. At these wavelengths, the surface is fully reflecting and no special oil films would be required. This is a big plus in practice. IR can also be used as the light source in the embodiments depicted in FIG. 6/7 as well. Solid state or other efficient point IR sources can also be used.

An advantage of the invention is that the operator can view the scanned reflected information coming back from the retroreflector, either through the beam splitter or by viewing slightly off axis of the incident beam. This permits him to visually see exactly what the detector is looking at, to confirm what the electronics is seeing. In this case, it is often advantageous to slow the mirror scan down.

For some flaws, it is desirable to rotate the sensor scan direction and pass over the flaw again to confirm its existance and description.

It is noted that in FIG. 3, the scan on the panel surface need not be back and forth, but can for example be circular, spiral, x shaped, etc. The circular scan offers an advantage in that it produces a smooth signal output with no turnaround point which is useful for taking derivatives. A circular sweep, for example, can get close to certain panel features and has no signal discontinuities which are disturbing to sensitive circuits. However, a rotating faceted mirror or oscillating mirror scan is the preferred means of generating scans in general, which are preferably parallel to one of the major axes of the panel.

All wavelengths visible, UV and IR of electromagnetic radiation are possible for an illumination source. HeNe or semiconducting diode lasers are preferred but conventional sources or other lasers can be used.

A further advantage results from the fact that the light can be focussed or defocussed via optional lens 240 onto the panel to a greater or lesser degree depending on what size flaw resolution is necessary. A raw laser beam (e.g. 0.050" wide) may be sufficiently small to detect high frequency variations due to "orange peel" in the painting process itself or to discern scratches, small pits and pimples, etc. A defocussed beam will only resolve slower changes in the panel and provide more signal to noise for low spots etc.—at a price of dimished scratch determination. This permits the system to be optimized for the case at hand. Often, a dual system is desirable. Such a dual system could utilize two beams having different spot sizes, or use a single beam to make one complete panel analysis and then change the spot size of the single beam and rescan. In addition, sequential scans can be with different sizes by turning lasers on and off.

In an embodiment utilizing two simultaneous beams and two detector units, the two beams are each of a different wavelength such that filters in front of each detector unit can separate one from the other. Alternatively, they can be staggered in position such that one detector only sees one or the the other. (One beam is slightly ahead of the other but driven by same scanner—if sufficiently far ahead, no wavelength discrimination is required. Indeed, both could be derived from the same laser.)

A different lens can be utilized to form each beam, one for example to blow the beam up a little bit to cause it to average over ripples in the surface due to orange peel etc. and the other one focussed down in order to see scratches.

Therefore, not only can two spatial sensitivities be defined during a simultaneous scan, but the beam and detector channel looking at the larger surface zone can be used as a reference level detection for the smaller detected zone if they are both looking at the same section of the surface at the same time (or suitably time delayed to create the same effect).

Note that a line array of light emitting diode light sources or fiber optic light sources can be used instead of a sweep for illumination. Since these would likely be fixed in location, the resolution would be a function of the spacing. However, flaw discrimination is still possible. For this version, a TV or other 2 axis scan camera is required since the sources are displaced, as is then the retroreflection. A CRT spot swept across its faceplate also provides such a source.

Figure 6A:
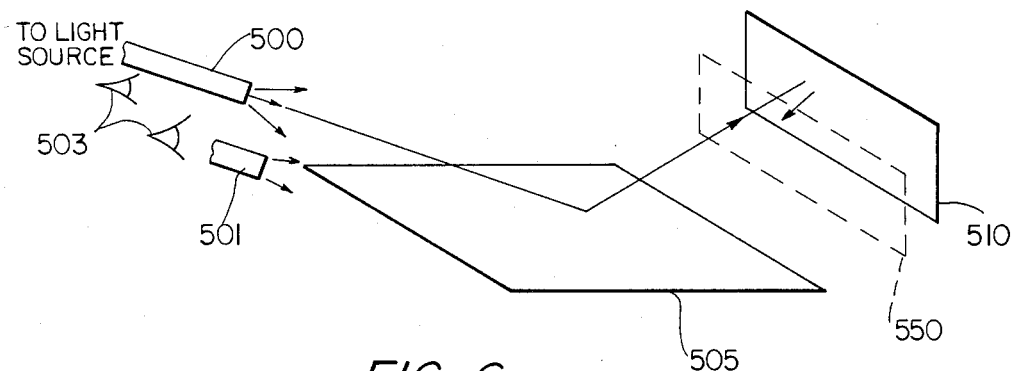
FIG. 6a illustrates a retroreflective embodiment using a point source and visual detection.

An important alternative embodiment in this invention is a manual version depicted in FIG. 6a. This embodiment uses a substantially point light source 500, such as a fiber optic end connected to a halogen bulb (not shown) at the other end, near the operator's eyes 502 for illuminating the panel 505. The operator views the light returning from the retroreflector 510 and off of the panel. With one eye, defects appear as dark spots on the panel. With 2 eyes, a kind of stereo occurs. For maximum results, two illumination light sources (e.g. 500 and 501) are arranged above or below each of the operator's eyes. This permits him to have the highest signal levels at each eye (since there is no angular difference between such source and the respective eye). The retro effect is so directional that the two sources don't interfere.

The effect produced is truly startling. To a die or stamping person it is much like when one sees a hologram for the first time. From a distance L2 of say 3 meters and L1=2 meters on a painted or well highlighted panel, all of the low spots and other localized geometric distortions and imperfections in the panel appear instantly visible—even ones that are less than 0.01 mm deep This effect has far reaching implications besides the use on panels themselves. For example, it can immediately be used to analyze painted cars on the line in final inspection. Second, it can be used on suitably prepared wood die models or clay models to see such distortions before they are scanned for CAD data. Third, it can be used to analyze dies and molds, male or female, and instantly see where material needs to be removed to make a smooth, good looking surface.

Substantially point light sources can be, for example, LED's, incandescent bulbs (e.g. a grain of wheat "bulb") or fiber optic ends with remoted light sources. Broad light sources such as florescent tubes can less preferably be used. These work if the tube is parallel to the surface. The retroreflecting screens or painted retroreflecting surfaces preferably surround the inspection zone for minimum inconvenience in the inspection process and to maximize signal to noise levels.

The inspector seeks the maximum defect sensitivity position and can move his viewing angle to achieve the best signal to noise response. Note that the light source(s) can be located on glasses, a helmet or a head fixture so as to easily move with the operator while keeping the sources near the eyes to allow for maximum retroreflective operation. Measuring reticles such as 535 (see FIG. 6b) or other aids superimposed in the operator's vision can aid in defect size evaluation.

Figure 6B:
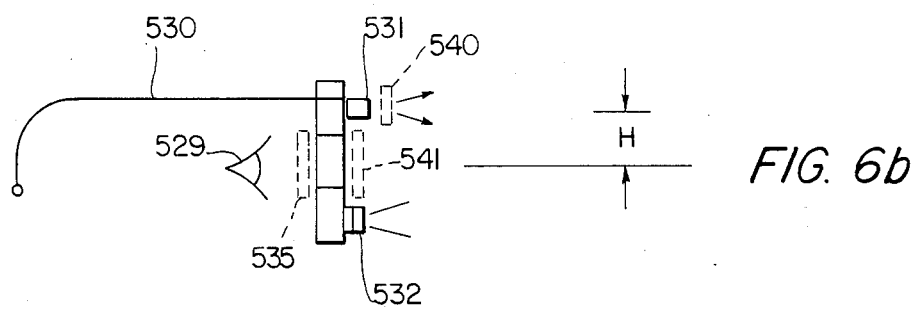

FIG. 6b illustrates a pair of eyeglasses provisioned according to the invention. The frame 530 has holes in it for vision with the eye 529 (only one eye shown for clarity). Light source 531 is located on the rim as is an optional second or other additonal source 532 for this eye. Optionally, a ring light source(s) surrounding the (or each) eye can be used which gives the most even illumination.

Where highlight oil is used on bare metal, it is often desirable to polarize the outgoing light from source 531 with a polarizer 540 and to use a crossed polaroid 541 in front of the eye. By virtue of quarter wave plate 550 (shown in FIG. 6a), only retroreflected light is substantially allowed to be seen. Element 541 can also represent a defocussing or blurring device to smooth the image of minor droplet deviations in the highlight oil as discussed below.

Figure 7:
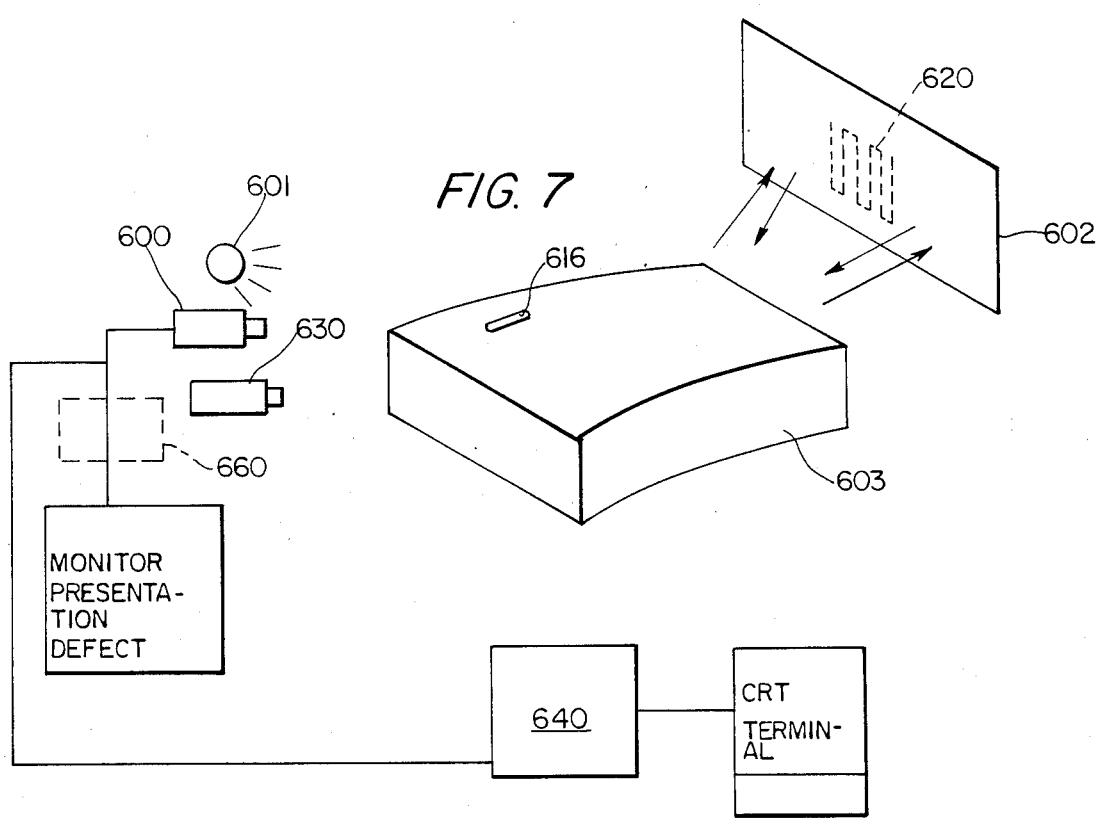
FIG. 7 illustrates an embodiment of the invention using one or more point sources with TV scan detection and a retroreflective grid option.

FIG. 7 illustrates a version of FIG. 6a operating on a female panel die in which the eye is replaced by a TV camera 600. In this case, a single light bulb souce 601 essentially illuminates the retroreflective screen 602 via die surface 603 and the TV camera views the retroreflective screen through reflection from the die. As in the human eye case, this is different than the version of FIG. 3, even though the retroreflector is used. In this case, it's not the beam position that varies since there is no beam per se. Due to the same geometric distortion factors, it is the concentration or diffusion of light due to the multiple individual "beams" from the point source that causes the image to be either dark or bright in certain areas depending on whether the flaw is or is not present.

For example, if there is no flaw present (e.g. a high spot 616 which should be removed) virtually all of the light going out from the point source hits the retroreflector (at an angle due to the compounding effect spreading from the light source and of the curvature of the panel) and comes back along the same path creating a nearly uniform light field image of the retroreflective screen on the TV camera. If, however, there is a defect as shown at high spot 616, the light does not come back in quite the same way and certain areas of the defect appear darker or lighter than the surrounding area. The degree of light field modification is proportional to the defect and the shape and the area of the defect can be immediately determined since the TV camera is capable of scanning the intensity field in two axes. Alternatively, a line scan camera can be moved relative to the surface just as in the case of the laser scan shown in FIG. 3 creating the same effect in time sequence.

For automatic detection, it is desirable to compare light in the defect (instantaneous level) to its surroundings. A means for doing this is described in a U.S. Pat. No. 4,305,661 and configurations thereof.

It is noted again that the TV camera system has less apparent ability (at least with a modest signal processor) to determine defects than a human which is quite good at seeing subtle light intensity gradients and the like. Therefore, the background reflections from the surface itself can be a problem. In this case, crossed polarizers and a retardation plate can be used as in FIG. 3 and 6b to kill the direct back reflection from the panel. As in FIG. 3, this may limit the field of view of the camera since retardation plates larger than let us say one foot in diameter are relatively rare. Optics as in FIG. 3f can be used to expand the field. Other techniques such as discussed above relative to the FIG. 6b can also be used.

Just as in the visual case, a second TV camera unit 630 can be used to obtain a sort of binocular stereo image of the defect. In this case, each point of radiation in one image is correlated to the same point in the other image particularly in the defect zone. This can be used to automatically calculate the depth of the flaw condition.

It is noted that the commercially available image processor computer 640 hooked to the TV camera can be used to analyze the area, shape, and intensity characteristics of the defect images in order to determine defect parameters. The TV camera can also be used with the visual inspection and then bore sighted with the direction of view of the visual inspection to provide a digitized analysis and quantitative output of the defect being observed (as in a gunsight reticle). In this mode, the operator looks at the panel with glasses as shown in FIG. 6b and the TV camera then automatically digitizes those flaws desired just by "looking" at them.

A suitable image processing computer to find display or quantify flaw areas, shapes, parameter outlines, and other parameters is a Machine Intelligence Co. Model 100, a Machine Vision International Co. Genesis 2000, or a GE Optimation II processor. The latter two are high speed and capable of realtime operation. For high speed measurement on moving parts (e.g. paint cans moving on a line), strobe illumination using a flashed Xenon source for example can be used to "freeze" the image for later analysis.

Note too that a videotape unit 660 can be optionally used to record panels or cars passing a line location for later analysis either visually or automatically. This allows a more relaxed human analysis (e.g. in an office) or a higher power large remote computer to be brought to bear on the image defect analysis—e.g. on the 3rd shift so statistical data would be available in the morning on the previous day's production.

Another embodiment of the invention related to FIG. 1 but using the retroreflective idea presented in FIG. 3 etc. is also shown in FIG. 7.

In this optional case, however, one or more edges of a grid or grille of parallel opaque lines or dots 620 are utilized. The grid or grille is placed in front of the retroreflector 602, or conversely the grid or grille is made out of retroreflective material and is used as the retroreflector. This grid then acts very much [for example, at least in the grille or grid case] like the grille or grid described in FIG. 1 except for the fact that it is illuminated retroreflectively through the panel. The dots simply represent the grid intersection points. There is a statistical evidence that dot image centroid shifts due to defects can be better defined than lines.

The line or grid embodiment of FIG. 7, while related to the FIG. 2 embodiment, differs in that it uses the point of light being directed back from the surface. The point of light is seen as coming from a side opposite from the sensor, but it is actually being illuminated from the sensor side. In short, while it is related to the FIG. 1 embodiment, it however is vastly simpler and more efficient to produce such an effect. Contrast is also much better. One needs only to have a small light source and a retroreflective screen with grids and indeed in this case the screen can be one of the walls of a particular area surrounding the place where the analysis is to take place. No particular lighting structure or anything else is required and the power levels required are quite small. This is because the light and the camera unit are at substantially the same location. Light is thus not required to light the whole room in order to be seen from a camera unit. Deviations in the panel are also enhanced by the effects of the double reflection. The edge points shift similar to the spot image of FIG. 3. Note that the edge deflections are easy to monitor with a TV camera. Just as in FIG. 6a, if one is 10 ft. away, the whole panel can be seen superimposed over what are the grid lines which are geometrically distorted locally in the presence of defects in surface form.

Figure 8:
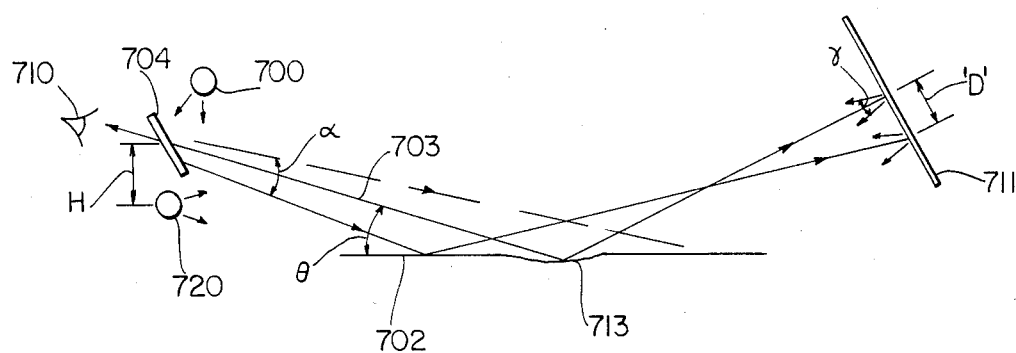
FIG. 8 illustrates a reflection in the FIGS. 6 and 7 embodiments.

FIG. 8 illustrates one mechanism for defect determination in the embodiments of FIGS. 6a and 7. As shown in FIG. 8, light is incident on a defect [in this case] whose extension is illustrated as being substantially in the direction of illumination rather than in the direction transverse thereto as was shown in previous embodiments. Light source 700 illuminates panel 702 along axis 703 via beam splitter 704. Human eye 710 views light from retroreflector 711 re-reflected back from panel 702 including defect 713 thereon.

As can be seen, light from the defect area is deflected away from the direct reflectance angle $\theta$ by the sloped walls of the defect. This results in a darker area 'D' on the screen than would otherwise have been the case, and with light redistributed to create a brighter area around the dark area.

Because the distance L2 of the source to the defect is typically much larger than the defect size itself, the subtended illumination angle of the defect area is typically smaller—i.e. the illumination is nearly parallel. Thus little "filling in" of the dark or light zones so created occurs, and the eye or other detector sees this effect. The zone 'D' is not completely black, however, as the eye is coincident with the illumination axis and the only light not returning to the eye is that which is re-emitted by the screen over a nonzero angle $\gamma$ and which hits the normal surface, for example, rather than passing right back through the same sloped surface of the defect.

The same sort of effect also occurs in the direction perpendicular to the plane of the drawing.

Now let us consider the effect of placing the light source off the angle of view as with light source 720. In this case, much less light from the sloped edge of the defect farthest from the eye can reach the edge and it thus appears darker, accentuating the indication. This is desirable in many cases.

Let us think now of how the automatic sensing of the invention can be utilized in stamping, molding or body plants.

Figure 13:
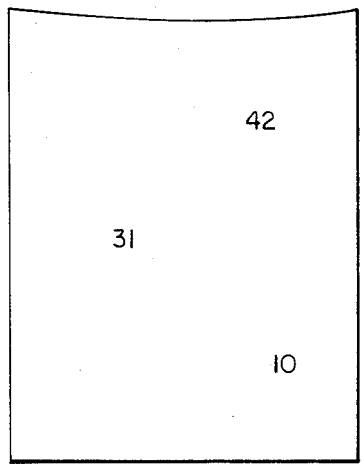
FIG. 13 illustrates a computer defect readout according to the invention.

FIG. 13 of the referenced U.S. Pat. No. 4,394,683 illustrates panels coming along the line. This is a typical arrangement for fixed sensors looking at panels coming off a press. In other installations, however, the panel might be in stationary motion or moving and a robotic arm is used to position the sensor unit. The checking of panels of this type can be done in two ways according to the present invention. The arm can actually sweep the sensor unit if it is capable of good uniform motion or conversely motorized tooling at the end of the arm can be used to make the sweep with the robot actually in a fixed position (which can be easier to program). Similarly, because of the properties of the retroreflective material, a two axis sweep can be utilized where the unit scans the surface with a 2 mirror sweep that raster scans. For example, motor 260 drives a planar mirror 261 (dotted lines) in FIG. 3 to provide a sweep in the y direction as well.

Figure 9:
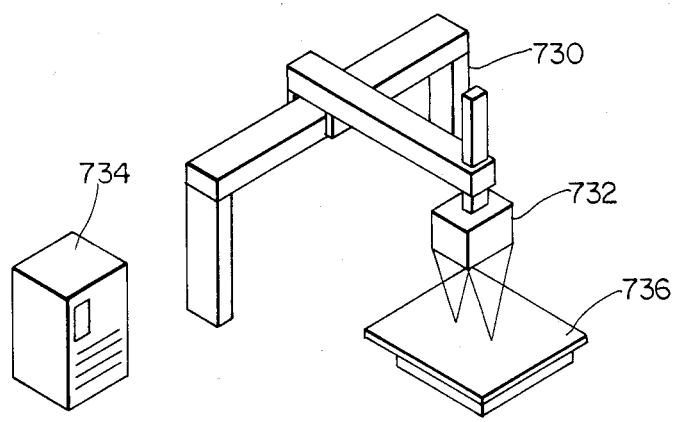
FIGS. 9–12 illustrate in-line or off-line plant applications of the invention.

FIGS. 9 to 12 illustrate several applications to plant use. Depicted in FIG. 9 is a robot 730 (in this case a gantry type Westinghouse 6000) and a scanned single sensor unit 732 comprising a retroreflective material sender and receiver along the lines of FIG. 3. This sensor can optionally further employ a scanning capability in the y axis using a 2 axis mirror scan or conversely a motor drive on the end effector tooling of the robot. The robot can be programmed using programming consol 734 to inspect numerous different types of panels 736.

The signal data from the sensor can be fed back to help maintain the standoff distance from the part or additional sensors added for this purpose if necessary.

Figure 10:
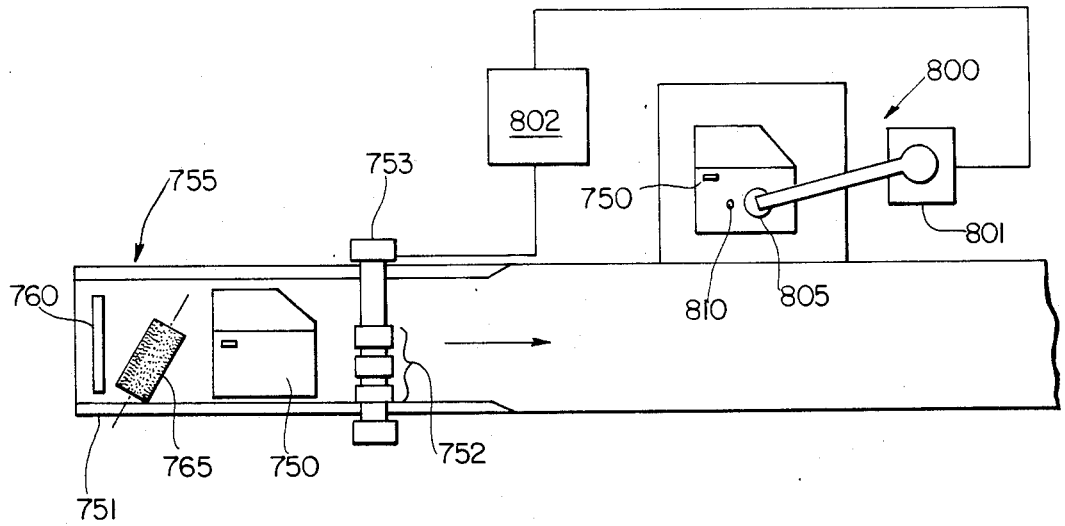

FIG. 10 illustrates a multiple fixed sensor unit according to either FIG. 3 or FIG. 7 in which car doors 750 move on a conveyor 751 underneath the sensor unit 'nest' 752 on frame 753. In this case, an automatic highlighter 755 is employed using a combined spray 760 and brush 765 operation.

Also illustrated in this figure is an automatic reject of defective panels to a robotic repair station 800. A robot 801, taking signals from the defect readout 802, picks up a disc grinder 805 or other tool and grinds down and feathers the defect 810. After doing so, the panel is fed back to the inspection station and reinspected to determine if it is now okay.

Figure 11A:
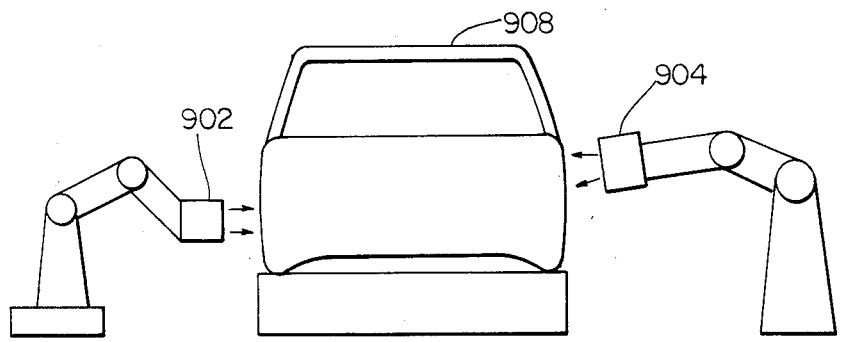
Figure 11B:
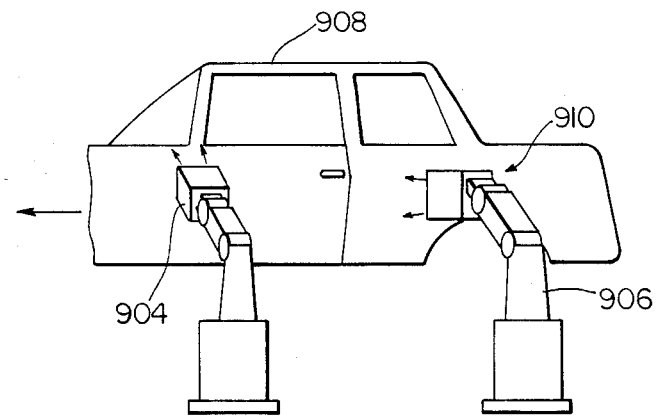

FIGS. 11a and 11b illustrate the use of robot mounted units 902 and 904 to scan a complete body-in-white 908 at a fixed position on-line. A robot highlighter 906 is employed using a brush/spray end effector 910 coordinated with the scan to always present 'streaks' if any, parallel to the direction of scan. A similar version can operate on finish painted cars where no highlight is required. Note that inspection of panel gap and mismatch can also be accomplished using a light section triangulation sensor carried by the robot as well.

Figure 12:
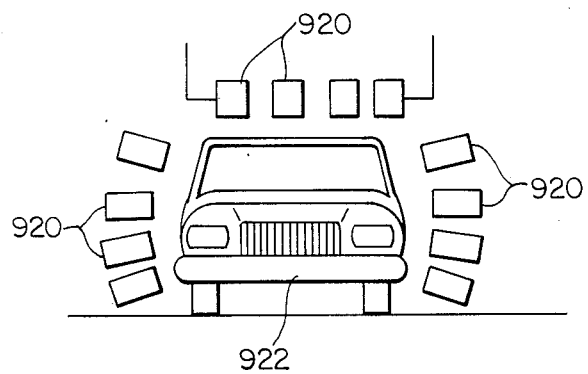

FIG. 12 illustrates an in-line version of the present invention for use on finished (painted) cars comprising fixed sensors 920 positioned to view the car 922 in-line. The large standoff and range of the retroreflective sensor types is a big advantage here allowing line motion to be cleared in most cases.

It is noted that this invention is useable not only on car body, appliance, and other panels to see defects thereon, but also on the dies, the wood models, clay models, molds and other formed parts or artifacts that are used in the sheet metal plastic and body building process. The invention is used to determine defects in form of these products and keep them from being propagated into the final product—e.g. the painted car.

Clearly, if one can see the small flat spots and other minute localized errors of form in the dies, one knows therefore where to take off the material, and how much to take off in the quantitive sense to make the die right. The same holds true even before the die process where wood models are used so that the models themselves can be checked to make sure that they don't have any errors which are then traced into machines that make the dies and resulting in great waste.

Clearly, to make the invention work, one has to have the surfaces sufficiently reflective. This means coating the wood, clay or metal with something, either oil, wax, reflective paper or some other material that can make it sufficiently reflective. Generally, it is desired also that the coating material be easily removeable.

It is particularly interesting to see the local form errors of dies and then look at the panels that are produced by them to correlate the defects, etc.

In the FIGS. 6 and 7 apparatus, it is further noted that to suppress the effect of ripple on the surface whether it be from orange peel, highlight oil, elephant hide on plastic, grain on plastic, or whatever, one can do several things:

1. Purposely blur the image as through defocussing. This is not necessarily effective in all cases as some of the depth of focus is very large in this system.

2. Utilize an oscillating glass to purposely mechanically blur the image by moving it. This effectively smears over the highlight on the screen making an average signal. However, it also can clearly move the radiant images as well as can the previous blurring.

3. Use a diffusing screen through which the images are viewed and which does not allow one to focus clearly on the highlight droplets.

4. Utilize (as in the FIG. 3 apparatus) computer filtering and processing to process the signals. For example, all lower frequency signals can be removed through AC coupling and all high frequency signals can be removed except those exhibiting certain characteristics, for example, showing the typical look of either a large deviation or a one sided or bi-directional slope of a dent.

In utilizing the invention, one can also make a rapid scan of the surface in hardware to identify that there is a suspected presence of a defect and then analyze the same signal which has been digitized through a software program at a relatively more leisurely pace to make a better evaluation. This can be going on while continued further sections of the panel are being scanned since one does not expect to find too many defects during the total scan.

Conversely, one can simply scan the panel and come back to those areas with suspected defects and simply dwell on them. This in effect then does not require a memory since one can just sit over the defect once it's found and analyze it. Since computer memory nowadays is cheap, however, it seems just as logical to read it in and keep going while analyzing it as the other data is being streamed in.

It is important to think of the possible ways of looking at this data. As one comes up next to a flawed area near a character line or what have you on the panel that one does not wish to see, one has to have some way of stopping the scan of the unit so that this is not picked up as a flaw. This can be done by simply storing the computer coordinates of the zones on the panel which are not to be looked to and blocking those out in the memory after one reads the scan in.

The other thing that can be done is to simply use the edge of the scan to see such flaws and come in with a precise triangle wave fed signal that allows one to back right up against the surface. Alternatively, one can rotate the sensor head so that the scan is parallel to the character line or what have you and scan across a flaw in that direction coming up right next to it. It is noted that with good highlighting or paint finish, one does not have to worry too much about the scan direction and such rotation is quite feasible. It's only in the case where the highlighting is poor and streaky that one really needs to scan parallel to the streaks.

To help the cause of highlight oil spreading out, one should, wherever possible, have a time delay built in between the application of highlight oil and the inspection, preferably at least 10 seconds or more.

It is noted that the retardation plates and polarizers are not as necessary at the lower angles as they are at the higher angles utilized for best performance. In other words, at low angles direct reflection back from the panel surface, be it paint or whatever, is less.

The processing described in FIG. 5a for seeing the rate of change of slope has been successfully used in finding low spots as shallow as 0.0002 inches (0.005 millimeters) in depth. Such low spots are, however, typically in the range of 0.0002 to 0.0025 inches in depth and generally the size of between one inch (2.5 cm) and 4 inches (10 cm) in overall width.

FIG. 13 illustrates a computer printout according to the invention.

In operating the invention, it has been found that spreading the beam in the scan direction using a cylinder lens, such as the optionally provided lens 240 shown as dotted lines in FIG. 3, spreads the beam in the scan direction and helps to improve the performance on low spots while providing a further averaging effect on the highlight conditions. However, at the same time, use of such a cylinder lens tends to mask smaller defects such as small dirt pimples and the like. In this case, it can be desirable to have a system which makes a scan in one pass using a cylinder lens (or another method of spreading the beam) and on the return pass does not use it, thereby giving two sensitivities, or optical intergrations, in the direction of scan. Such a programmable device can be a solenoid to simply pull the cylinder lens in and out, or, at higher speed, an acousto-optical modulator to spread the beam on one pass and do nothing to it on the next.

It is also possible to provide such signal averaging manipulations in hardware circuits or computer software 290 as shown in FIG. 3. Hardware signal averaging can be used like that of U.S. Pat. No. 4,305,661 using tapped analog delay lines which allow the instantaneous signal to be compared to the average of sections of signal spaced ahead and/or behind in time.

A programmable correlator can also be used to correlate the signals of the different defects to actual signals. For example, low spots, dings, and dents all have the positive and negative going slope signals but at different widths. Therefore, while the second derivative circuit works on those where the slope is high, those of less slope can be obtained from correlation, either using a hardware correlator or preferably one tuneable at different frequencies to allow the right match to the signal in question to be obtained. In addition, a computer software correlation can be made if time permits.

Correlation is not the only way to see such signals but it does allow the known signatures of the defect to be matched.

Relative to the visual and TV versions of FIGS. 6 and 7, it has been found that in some cases with the observer looking directly through with the lights, either surrounding the eye or placed very near the eye, that this does not give as good a view as with the light slightly displaced, for example, in the vertical direction looking at the panel hood in FIG. 6a.

For example, with a vertical displacement H as shown in FIG. 6b, let us say with the light for example 2 inches above or below the eye, the light power coming back from the retroreflector is considerably decreased at let us say L2=10 feet away because one is off the retro angle somewhat. However, there is a definite shadowing effect that takes place under these conditions which tends to accentuate the defects, often providing a clearer view (as the direct view can wash out in some cases).

For some purposes, it could be desirable to switchably view the flaw with the light along the axis and at an off-axis position. In this case, two sets of lights can be used: one central, and one off axis. The two sets of lights are then simply switched. This switching can be automatic or manual. Conversely, two TV cameras can be used with a single light with the two cameras spaced, for example, and switched.

Figure 14A:
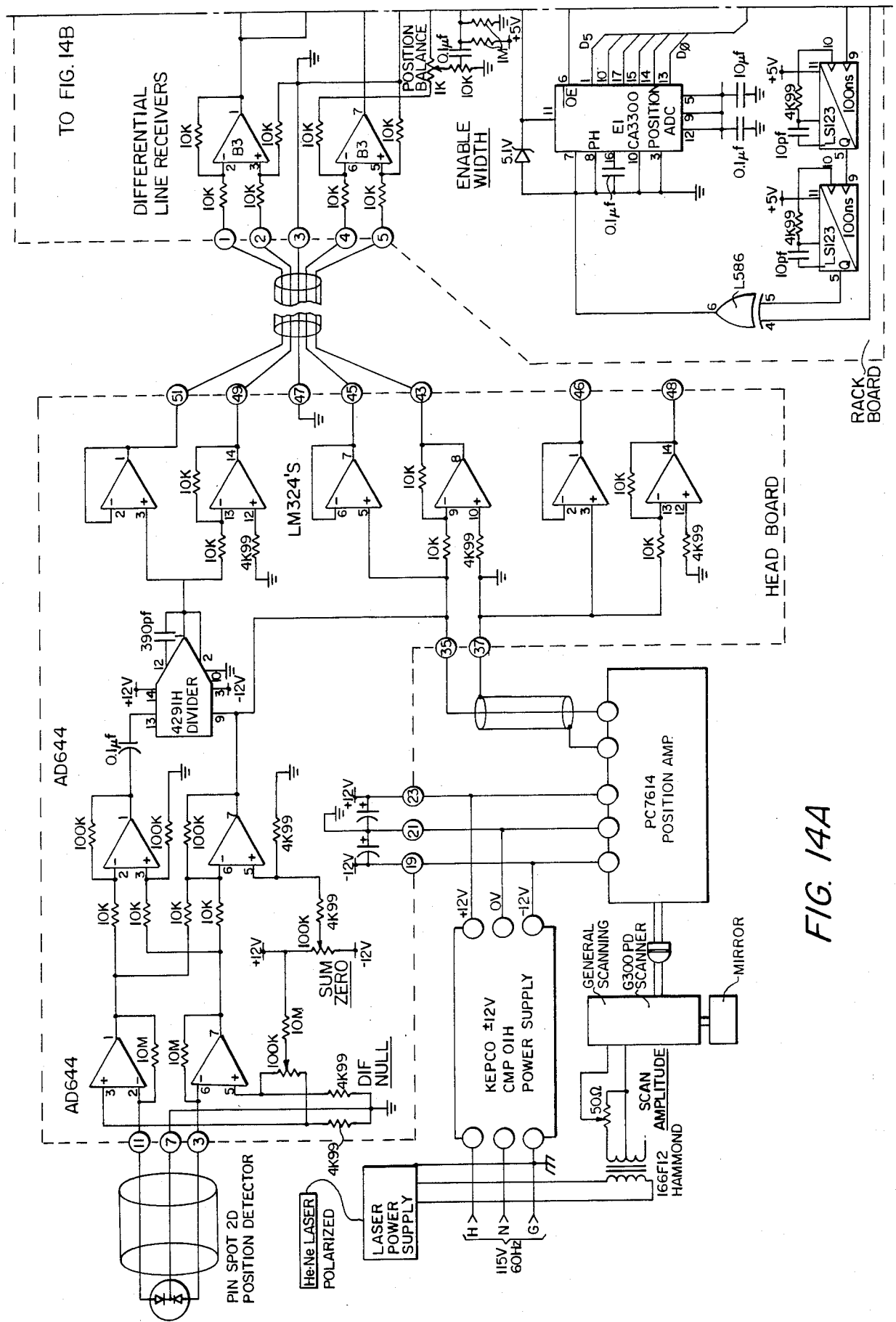
FIGS. 14a and 14b illustrate circuit processing according to the invention.
Figure 14B:
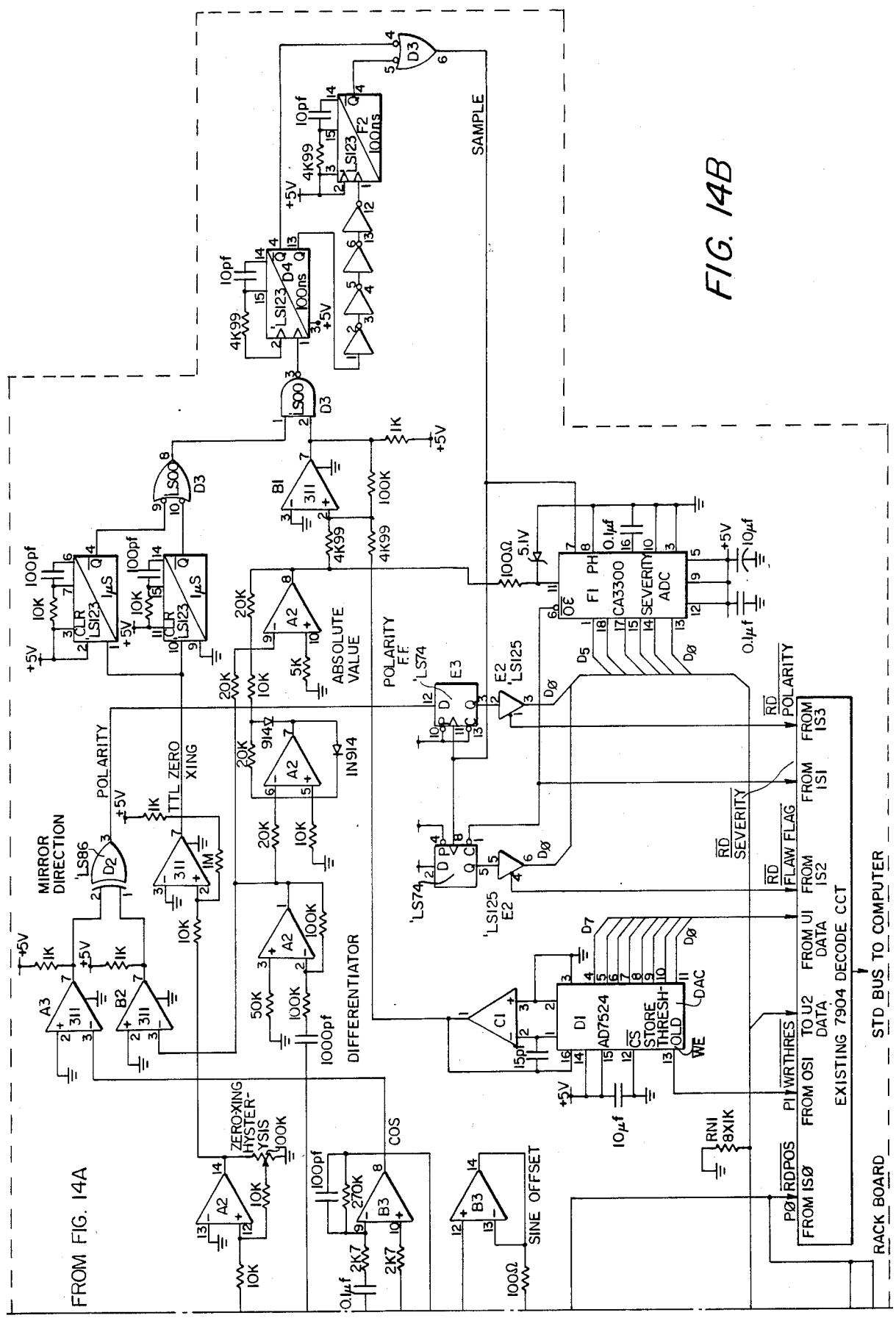

FIG. 14 illustrates a circuit capable of defect discrimination in the FIG. 3 embodiment, which is used to generate the readout of FIG. 13.

As shown in FIG. 14, the returned laser light is imaged on the UDT Pin Spot 2D photodetector (photodetector 215 in FIG. 3) typically forming a spot. The detector's output currents are converted to voltage in the first AD644 halves. The voltages are then amplified by the second set of 644's as well as being combined.

Two outputs applied to the 4291 H Divider are the "sum" of the light striking the detector, and the "difference" between the halves of the detector.

The divider's output (Difference/sum) is the power compensated "position" of the light spot on the detector.

The spot position signal and the beam steering mirror's (mirror 202 in FIG. 3) position signal are both sent to the Rack board for further processing.

The mirror's position is differentiated to give the COS of mirror position. This signal is then applied to a zero crossing detector to obtain a mirror "direction" signal. The original SIN signal is sent to an Analog to Digital converter (ADC) so that the computer can read the position of the mirror. A "position balance" potentiometer is used to correct for small delays through the differentiator and the "enable width" control allows digitization of only a part of the mirror's swing.

The image spot position signal is sent to a zero crossing detector as well as a differentiator. The zero crossing signal is sent to a pair of monostables, used to generate a pulse on every zero-crossing no mater which direction.

The differentiated spot position signal is sent to an absolute value amplifier. This stage's output is applied to an ADC to allow the computer to read the apparent "severity" of the defect on the surface being inspected. This "severity" signal is then compared to a threshold which is computer generated from a DAC. The comparator's output is then used to gage the zero crossing pulses. Only when the spot position signal is crossing through zero and the differentiated position is sufficiently large, does the "Defect found" flip flop get set.

The computer then reads the "mirror position" and the "severity" from the circuit, and stores these values as well as the "polarity" and scan line number into a data array for further processing.

The "polarity" signal is generated by exclusive ORing the "mirror direction" and a signal generated by comparing the "differentiated spot position" with zero volts.

Because of the quirk in the inner workings of the ADC's it is necessary to apply two pulses in quick succession to their clock inputs in order to cause a conversion, hence the extra monostables and gates.

The computer generates a list of flaws giving the x and y locations, the severity, the type (in or out dents) the flaw length and a rating based on length "severity". The "severity" is then plotted against xy coordinates.

What is claimed is:

1. A method of inspecting a surface comprising the steps of:
   illuminating an extensive area of the surface by directing light onto the surface area in such a manner that light is reflected therefrom;
   providing a retroreflective member comprising a large number of small retroreflective elements in a position such that light reflected from the extensive illuminated surface area impinges thereon, is then returned to the illuminated surface area, and is re-reflected therefrom;
   imaging light re-reflected from the extensive illuminated surface area; and
   detecting dark or bright areas in the imaged light, the dark or bright areas being indicative of a characteristic of the extensive illuminated surface area.

2. A method according to claim 1 wherein said illuminating is effected with light from a divergent light source.

3. A method according to claim 2 wherein said divergent light source comprises a point light source.

4. A method according to claim 1 wherein said imaging and detecting are effected by visual observation.

5. A method according to claim 1 further comprising recording said imaged light.

6. A method according to claim 5 wherein said detecting comprises detecting said dark or bright areas in said recorded imaged light.

7. A method according to claim 2 wherein said illuminating is effected from a location displaced from the axis of light detection.

8. Apparatus for inspecting a surface comprising;
   illuminating means for illuminating an extensive area of a surface by directing light onto the surface area in such a manner that light is reflected therefrom;
   a retroreflective member comprising a large number of small retroreflective elements positioned relative to the surface such that light reflected from the extensive illuminated surface area impinges thereon, is then returned to the illuminated surface area, and is re-reflected therefrom;
   imaging means for imaging light re-reflected from the extensive illuminated surface area; and
   detecting means for detecting dark or bright areas in the imaged light, the dark or bright areas being indicative of a characteristic of the extensive illuminated surface area.

9. Apparatus according to claim 8 wherein said illuminating means comprises a divergent light source.

10. Apparatus according to claim 9 wherein said divergent light source comprises a point light source.

11. Apparatus according to claim 8 further comprising means for recording said imaged light.

12. Apparatus according to claim 11 wherein said detecting means comprises means for detecting said dark or bright areas in said recorded imaged light.

13. Apparatus according to claim 8 wherein said illuminating means is positioned in a location displaced from the axis of light detection.

14. A method of inspecting a surface comprising:
   illuminating an extensive area of a surface of an object with light from a divergent light source;
   providing a retroreflective member comprising a large number of small retroreflective elements in a position such that light reflected from said illuminated surface is returned to the illuminated surface and re-reflected therefrom; and
   imaging said re-reflected light.

15. A method according to claim 14 wherein said imaging is effected by visual observation.

16. A method according to claim 15 wherein said visual observation is effected from a vantage point which is substantially on the axis of illumination of said surface.

17. A method according to claim 15 wherein said visual observation is effected from a vantage point which is displaced from the axis of illumination of said surface.

18. A method according to claim 14 further comprising recording the imaged light.

19. A method according to claim 14 wherein said divergent light source comprises a point light source.

20. Apparatus for inspecting a surface comprising:

light source means for illuminating an extensive area of a surface of an object with divergent light;

a retroreflective member comprising a large number of small retroreflective elements, said member being positionable such that light reflected from a surface illuminated with divergent light from said light source means is returned to the illuminated surface and re-reflected therefrom; and means for imaging said re-reflected light.

21. Apparatus according to claim 20 wherein said imaging means is positioned at a vantage point substantially on the axis of illumination of said surface.

22. Apparatus according to claim 20 wherein said imaging means is positioned at a vantage point displaced from the axis of illumination of said surface.

23. Apparatus according to claim 20 further comprising means for recording the imaged light.

24. Apparatus according to claim 20 wherein said divergent light source comprises a point light source.

25. A method of visually observing a geometric distortion in a surface comprising:

illumiating an extensive area of a surface of an object;

providing a retroreflective member comprising a large number of small retroreflective elements in a position such that light reflected from said illuminated surface is returned to the illuminated surface and re-reflected therefrom, said re-reflected light comprising bright or dark areas indicative of a geometric distortion in said surface; and visually observing light re-reflected from the illuminated surface to observe the surface and a geometric distortion therein.

26. A method according to claim 25 wherein the step of visually observing said surface is effected from a vantage point which is substantially on the axis of illumination of said surface.

27. A method according to claim 25 wherein the step of visually observing said surface is effected from a vantage point which is displaced from the axis of illumination of said surface.

28. A method according to claim 25 wherein said illuminating if effected with light from a divergent light source.

29. A method according to claim 28 wherein said divergent light source comprises a point light source.

30. Apparatus for rendering visible a geometric distortion in a surface comprising:

means for illuminating an extensive area of a surface of an object; and a retroflective member comprising a large number of small retroreflective elements;

said retroreflective member being positioned in a location such that light reflected from said illuminated surface is returned to the illuminated surface and re-reflected therefrom, said re-reflected light comprising visible bright or dark areas indicative, under visual observation, of a geometric distortion in said surface.

31. Apparatus according to claim 30 further comprising means for recording an image of said re-reflected light comprising said bright or dark areas.

32. Apparatus according to claim 31 wherein said image recording means is positioned at a vantage point which is substantially on the axis of illumination of said surface.

33. Apparatus according to claim 31 wherein said image recording means is positioned at a vantage point which is displaced from the axis of illumination of said surface.

34. Apparatus according to claim 30 wherein said illuminating means comprises a divergent light source.

35. Apparatus according to claim 34 wherein said divergent light source comprises a point light source.

36. A method of detecting a geometric distortion in a surface comprising:

illuminating a surface of an object with light such that an area of such surface is illuminated, said area being substantially larger than a geometric distortion to be detected;

providing a retroreflective member comprising a large number of small retroreflective elements in a position such that light reflected from said illuminated surface is returned to the illuminated surface and re-reflected therefrom; and detecting light re-reflected from the illuminated surface, said re-reflected light comprising detectable dark or bright areas indicative of a geometric distortion present in the illuminated surface.

37. A method according to claim 36 wherein said object comprises an automotive body panel and wherein substantially the entire area of said body panel is illuminated.

38. A method according to claim 36 wherein said illuminating is effected with a divergent light source.

39. A method according to claim 38 wherein said divergent light source comprises a point light source.

40. A method according to claim 36 wherein said detecting comprises visually observing said re-reflected light.

41. A method according to claim 36 wherein said detecting is effected from a vantage point displaced from the axis of illumination of said surface area.

42. A method according to claim 36 wherein said detecting comprises recording an image of said re-reflected light.

43. Apparatus for detecting a geometric distortion in a surface comprising:

means for illuminating a surface of an object with light such that an area of said surface is illuminated, said area being substantially larger than the area of a geometric distortion to be detected;

a retroreflective member comprising a large number of small retroreflective elements;

said retroreflective member being positioned such that light reflected from said illuminated surface is returned to the illuminated surface and re-reflected therefrom; and means for detecting light re-reflected from the illuminated surface, said re-reflected light comprising detectable dark or bright areas indicative of a geometric distortion present in the illuminated surface.

44. Apparatus according to claim 43 wherein said illuminating means comprises a divergent light source.

45. Apparatus according to claim 44 wherein said divergent light source comprises a point light source.

46. Apparatus according to claim 43 wherein said detecting means is positioned at a location displaced from the axis of illumination of said surface.

47. Apparatus according to claim 43 wherein said detecting means comprises means for recording an image of said re-reflected light.

48. A method of inspecting a surface comprising:

illuminating a surface of an object with light;

providing a retroreflective member comprising a large number of small retroreflective elements in a position such that light reflected from said illuminated surface is returned to the illuminated surface and re-reflected therefrom; and detecting light re-reflected from the illuminated surface, said illumination being effected from a location displaced from the axis of light detection.

49. A method according to claim 48 wherein said detecting comprises visually observing said re-reflected light.

50. A method according to claim 48 wherein said illuminating is effected with a divergent light source.

51. A method according to claim 50 wherein said divergent light source comprises a point light source.

52. A method according to claim 48 wherein said detecting comprises imaging said re-reflected light and detecting dark or bright areas in the imaged light.

53. A method according to claim 52 further comprising recording the imaged light.

54. Apparatus for inspecting a surface comprising:

means for illuminating a surface of an object with light;

a retroreflective member comprising a large number of small retroreflective elements; that said retroreflective member being positioned such light reflected from said illuminated surface is returned to the illuminated surface and re-reflected therefrom; and means for detecting light re-reflected from the illuminated surface; a location said illuminating means being positioned at displaced from the axis of light detection.

55. Apparatus according to claim 54 wherein said illuminating means comprises a divergent light source.

56. Apparatus according to claim 55 wherein said divergent light source comprises a point light source.

57. Apparatus according to claim 54 wherein said detecting means comprises means for imaging said re-reflected light and for detecting dark or bright areas in the imaged light.

58. Apparatus according to claim 57 further comprising means for recording the imaged light.

* * * * *